(12) United States Patent
Gotschall et al.

(10) Patent No.: US 11,591,583 B2
(45) Date of Patent: *Feb. 28, 2023

(54) HIGHLY POTENT ACID ALPHA-GLUCOSIDASE WITH ENHANCED CARBOHYDRATES

(71) Applicant: Amicus Therapeutics, Inc., Philadelphia, PA (US)

(72) Inventors: Russell Gotschall, Doylestown, PA (US); Hung V. Do, New Hope, PA (US)

(73) Assignee: Amicus Therapeutics, Inc., Philadelphia, PA (US)

(*) Notice: Subject to any disclaimer, the term of this patent is extended or adjusted under 35 U.S.C. 154(b) by 0 days.

This patent is subject to a terminal disclaimer.

(21) Appl. No.: 17/665,179

(22) Filed: Feb. 4, 2022

(65) Prior Publication Data

US 2022/0162578 A1 May 26, 2022

Related U.S. Application Data

(60) Continuation of application No. 17/249,175, filed on Feb. 23, 2021, which is a division of application No. 16/252,505, filed on Jan. 18, 2019, now Pat. No. 10,961,522, which is a continuation of application No. 15/515,808, filed as application No. PCT/US2015/053252 on Sep. 30, 2015, now Pat. No. 10,208,299.

(60) Provisional application No. 62/135,345, filed on Mar. 19, 2015, provisional application No. 62/112,463, filed on Feb. 5, 2015, provisional application No. 62/057,842, filed on Sep. 30, 2014, provisional application No. 62/057,847, filed on Sep. 30, 2014.

(51) Int. Cl.
  *C12N 9/40* (2006.01)
  *A61K 48/00* (2006.01)
  *C12N 15/09* (2006.01)

(52) U.S. Cl.
  CPC .......... *C12N 9/2465* (2013.01); *A61K 48/005* (2013.01); *C12N 15/09* (2013.01); *C12Y 302/0102* (2013.01); *C12N 2510/02* (2013.01)

(58) Field of Classification Search
  CPC .. C12N 9/2465; C12N 15/09; C12N 2510/02; C12Y 302/0102; A61K 48/005
  See application file for complete search history.

(56) References Cited

U.S. PATENT DOCUMENTS

| | | | |
|---|---|---|---|
| 4,837,237 A | 6/1989 | Rohrschneider |
| 4,985,445 A | 1/1991 | Tsuruoka et al. |
| 5,011,829 A | 4/1991 | Hirsch et al. |
| 5,103,008 A | 4/1992 | Scudder et al. |
| 5,236,838 A | 8/1993 | Rasmussen et al. |
| 5,399,567 A | 3/1995 | Platt et al. |
| 5,472,969 A | 12/1995 | Platt et al. |
| 5,580,757 A | 12/1996 | Desnick et al. |
| 5,786,369 A | 7/1998 | Platt et al. |
| 5,801,185 A | 9/1998 | Platt et al. |
| 5,879,680 A | 3/1999 | Ginns et al. |
| 6,083,725 A | 7/2000 | Selden et al. |
| 6,118,045 A | 9/2000 | Reuser et al. |
| 6,210,666 B1 | 4/2001 | Miyamura |
| 6,225,325 B1 | 5/2001 | Jacob |
| 6,274,597 B1 | 8/2001 | Fan |
| 6,395,884 B1 | 5/2002 | Selden et al. |
| 6,451,600 B1 | 9/2002 | Rasmussen et al. |
| 6,458,574 B1 | 10/2002 | Selden et al. |
| 6,461,609 B1 | 10/2002 | Calhoun et al. |
| 6,465,488 B1 | 10/2002 | Butters et al. |
| 6,534,300 B1 | 3/2003 | Canfield |
| 6,537,785 B1 | 3/2003 | Canfield |
| 6,545,021 B1 | 4/2003 | Mueller et al. |
| 6,583,158 B1 | 6/2003 | Fan et al. |
| 6,589,964 B2 | 7/2003 | Fan et al. |
| 6,599,919 B2 | 7/2003 | Fan et al. |
| 6,696,059 B2 | 2/2004 | Jacob et al. |
| 6,916,829 B2 | 7/2005 | Fan et al. |
| 7,141,582 B2 | 11/2006 | Fan et al. |
| 7,351,410 B2 | 4/2008 | Van Bree et al. |
| 7,371,366 B2 | 5/2008 | Canfield |
| 7,396,811 B2 | 7/2008 | Lebowitz et al. |
| 7,560,424 B2 | 7/2009 | Lebowitz et al. |
| 7,655,226 B2 | 2/2010 | Van Bree et al. |
| 7,658,916 B2 | 2/2010 | Zhu et al. |

(Continued)

FOREIGN PATENT DOCUMENTS

| | | |
|---|---|---|
| EP | 1137762 B1 | 10/2008 |
| EP | 2020438 A1 | 2/2009 |

(Continued)

OTHER PUBLICATIONS

Courageot, M-P. et al. (2000) "a-Glucosidase inhibitors reduce dengue virus production by affecting the initial steps ofvirion morphogenesis in the endoplasmic reticulum" J Viral, 74:564-572.

(Continued)

*Primary Examiner* — Li N Komatsu

(74) *Attorney, Agent, or Firm* — Servilla Whitney LLC

(57) ABSTRACT

Recombinant human alpha glucosidase (rhGAA) composition derived from CHO cells that contains a more optimized glycan composition consisting of a higher amount of rhGAA containing N-glycans carrying mannose-6-phosphate (M6P) or bis-M6P than conventional rhGAAs, along with low amount of non-phosphorylated high mannose glycans, and low amount of terminal galactose on complex oligosaccharides. Compositions containing the rhGAA, and methods of use are described.

16 Claims, 18 Drawing Sheets

Specification includes a Sequence Listing.

(56) References Cited

U.S. PATENT DOCUMENTS

| | | |
|---|---|---|
| 7,785,856 B2 | 8/2010 | Lebowitz et al. |
| 7,858,576 B2 | 12/2010 | Lebowitz et al. |
| 7,910,545 B2 | 3/2011 | Meeker et al. |
| 7,981,864 B2 | 7/2011 | Lebowitz |
| 8,785,168 B2 | 7/2014 | Lebowitz et al. |
| 8,900,552 B2 | 12/2014 | Chen |
| 8,940,766 B2 | 1/2015 | Boyd et al. |
| 9,056,101 B2 | 6/2015 | Lockhart |
| 9,181,184 B2 | 11/2015 | Mugrage et al. |
| 9,186,420 B2 | 11/2015 | Koeberl |
| 9,303,249 B2 | 6/2016 | Valenzano et al. |
| 9,404,100 B2 | 8/2016 | Valenzano et al. |
| 2002/0049233 A1 | 4/2002 | Kararli et al. |
| 2002/0095135 A1 | 7/2002 | Meeker et al. |
| 2004/0180419 A1 | 9/2004 | Fan |
| 2004/0204379 A1 | 10/2004 | Cheng et al. |
| 2005/0058634 A1 | 3/2005 | Zhu |
| 2005/0244400 A1 | 11/2005 | Lebowitz et al. |
| 2006/0121018 A1 | 6/2006 | Lebowitz |
| 2006/0264467 A1 | 11/2006 | Mugrage et al. |
| 2007/0178081 A1 | 8/2007 | Fan |
| 2009/0117091 A1 | 5/2009 | Lebowitz et al. |
| 2009/0191178 A1 | 7/2009 | Zankel et al. |
| 2009/0203575 A1 | 8/2009 | Lebowitz et al. |
| 2010/0119502 A1 | 5/2010 | Do et al. |
| 2010/0260740 A1 | 10/2010 | Boyd et al. |
| 2010/0266571 A1 | 10/2010 | Lockhart et al. |
| 2011/0136151 A1 | 6/2011 | Wustman et al. |
| 2011/0189710 A1 | 8/2011 | Wustman et al. |
| 2011/0223147 A1 | 9/2011 | Lebowitz |
| 2011/0268721 A1 | 11/2011 | Do et al. |
| 2011/0300120 A1 | 12/2011 | Avila et al. |
| 2012/0064545 A1 | 3/2012 | Khanna et al. |
| 2015/0086530 A1 | 3/2015 | Greene et al. |
| 2015/0147309 A1 | 5/2015 | Parenti et al. |
| 2015/0258081 A1 | 9/2015 | Lukas et al. |
| 2016/0184410 A1 | 6/2016 | Chen |
| 2016/0243203 A1 | 8/2016 | Van Bree et al. |
| 2017/0056483 A1 | 3/2017 | Valenzano et al. |
| 2017/0298335 A1 | 10/2017 | Gotschall et al. |

FOREIGN PATENT DOCUMENTS

| | | |
|---|---|---|
| FR | 2861991 A1 | 5/2005 |
| JP | 2005523882 A | 8/2005 |
| JP | 2008525457 A | 7/2008 |
| JP | 2008545657 A | 12/2008 |
| JP | 2010525084 A | 7/2010 |
| JP | 2011512876 A | 4/2011 |
| WO | 00034451 A1 | 6/2000 |
| WO | 01019955 A2 | 3/2001 |
| WO | 03032907 A2 | 4/2003 |
| WO | 2004069190 A2 | 8/2004 |
| WO | 2005077093 A2 | 8/2005 |
| WO | 2006071613 A2 | 7/2006 |
| WO | 2006125141 A2 | 11/2006 |
| WO | 2008112525 A2 | 9/2008 |
| WO | 2008134628 A2 | 11/2008 |
| WO | 2009066069 A1 | 5/2009 |
| WO | 2009114679 A2 | 9/2009 |
| WO | 2010015816 A2 | 2/2010 |
| WO | 2010075010 A2 | 7/2010 |
| WO | 2010148253 A2 | 12/2010 |
| WO | 2011109600 A1 | 9/2011 |
| WO | 2012145644 A1 | 10/2012 |
| WO | 2013013017 A2 | 1/2013 |
| WO | 2013091897 | 6/2013 |
| WO | 2016054231 A1 | 4/2016 |

OTHER PUBLICATIONS

Cox, T. et al. (2000) "Novel oral treatment of Gaucher's disease with N-butyldeoxynojirimycin (OGT 918) to decrease substrate biosynthesis" The Lancet, 355:1481-1485.

Dale, M.P. et al. (1985) "Reversible inhibitors of 6-glucosidase" Biochemistry, 24:3530-3539.

Database Score SEQ ID No. 1 sequence in WO 2012145644A1. Retrieved from: http://score.uspto.gov/ScoreAccessWeb/viewSeqIdResult.htm, pp. 1-3; accessed Jan. 22, 2018, 3 pages.

Duke University Medical Center (1997) "Duke Obtains FDA Designation for Pompe Disease Therapy" Press Release, dated Sep. 2, 1997, 2 pages.

European Application No. 15845664.0, filed Apr. 6, 2017, by Amicus Therapeutics, Inc.: Supplementary European Search Report, dated Feb. 12, 2018, 13 pages.

Fryar, C.D. et al. (Oct. 2012) "Anthropometric Reference Data for Children and Adults: United States 2007-2010" National Center for Health Statistics. Vital Health Stat, Series 11, No. 252, 48 pages.

Genzyme Corporation (2010) Myozyme®. Highlights of Prescribing Information. Cambridge, MA: Genzyme Corporation, Jun. 2010, 3 pages.

Jeyakumar, M. et al. (1999) "Delayed symptom onset and increased life expectancy in Sandhoff disease mice treated with N-butyldeoxynojirimycin" Proc Natl Acad Sci USA, 96:6388-6393.

Khanna. R. et al. (2012) "The pharmacological chaperone AT2220 increases recombinant human acid aglucosidase uptake and glycogen reduction in a mouse model of Pompe disease" PLoS ONE, 7(7):e40776, 14 pages.

Kishnani, P. et al. (2017) "Duvoglustat HCl Increases Systemic and Tissue Exposure of Active Acid a-Glucosidase in Pompe Patients Co-administered with Alglucosidase a" Molecular Therapy, 25(5):1199-1208.

Klinge, L. et al. (2005) "Enzyme replacement therapy in classical infantile Pompe disease: results of a ten-month follow-up study" Neuropediatrics, 36(1):6-11.

Legler, G. and S. Pohl (1986) "Synthesis of 5-amino-5-deoxy-D-galactopyranose and 1,5-dideoxy-1,5-imino-D-galactitol, and their inhibition of alpha- and beta-D-galactosidases" Carbohydrate Res, 155: 119-129.

Mellor, H.R. et al. (2004) "Cellular effects of deoxynojirimycin analogues; uptake, retention and inhibition of glycosphingolipid biosynthesis" Biochem J, 381 :861-866.

Moreland et al., Lysosomal Acid alpha-Glucosidase Consists of Four Different Peptides Processed from a Single Chain Precursor, The Journal of Biological Chemistry, 2005, 280:6780-6791.

National Institutes of Heal TH Clinical Center (2002) Patient Education Materials: Giving a subcutaneous injection. Bethesda, MD: NIH Clinical Center, 3 pages.

Okumiya et al., Chemical chaperones improve transport and enhance stability of mutant a-glucosidases in glycogen storage disease type II. Mol. Genet. Metab. 90: 49-57 (2007).

Parenti et al., A Chaperone Enhances Blood a-Glucosidase Activity in Pompe Disease Patients Treated with Enzyme Replacement Therapy. Mol. Ther. 22(11 ):2004-2012 (2014).

Parenti, G. et al. (2005) "Alpha-Glucosidase Enhancement in Fibroblasts from Patients with Pompe Disease" J Inherit Metab Dis, 28(Suppl. 1): 193, Abstract 383-P.

PCT International Search Report and Written Opinion dated Jan. 6, 2016, in PCT/US2015/053252, 9 pages.

PCT International Search Report and Written Opinion dated Mar. 7, 2017, in PCT/US2016/069243, 10 pages.

PCT International Search Report and Written Opinion dated May 8, 2013, in PCT/US2013/029660, 8 pages.

PCT International Search Report and Written Opinion dated Oct. 1, 2013, in PCT/US2013/039215, 9 pages.

Platt, F.M. et al. (1997) "Prevention of Lysosomal Storage in Tay-Sachs Mice Treated with Nbutyldeoxynojirimycin" Science, 276:428-431.

Porto, C. et al. (2009) "The Pharmacological Chaperone N-butyldeoxynojirimycin Enhances Enzyme Replacement Therapy in Pompe Disease Fibroblasts" Mo/ Ther, 17(6):964-971.

Raben, N. et al. (2005) "Replacing acid alpha-glucosidase in Pompe disease: recombinant and transgenic enzymes are equipotent, but neither completely clears glycogen from type II muscle fibers" Mol Ther, 11 (1):48-56.

(56) References Cited

OTHER PUBLICATIONS

Ruvinov, S.B. et al. (1995) "Monovalent Cations Partially Repair a Conformational Defect in a Mutant Tryptophan Synthase a2 132 Complex (,8-E109A)" J Biol Chem, 270: 17333-17338.

SEQ ID No. 1 sequence in WO 2012145644 A1, from http://score.uspto.gov/ScoreAccessWeb/viewSeqIdResult.htm, pp. 1-3, accessed Jan. 22, 2018.

U.S. Appl. No. 14/379,131: Non-Final Office Action, dated Sep. 15, 2015, 13 pages.

Van Der Ploeg, At. et al. (1988) "Receptor-Mediated Uptake of Acid a-Glucosidase Corrects Lysosomal Glycogen Storage in Cultured Skeletal Muscle" Pediatric Research, 24(1 ):90-94.

Van Hove, J.L.K. et al. (1997) "Purification of recombinant human precursor acid a-glucosidase" Biochem Mol Biol Int, 43(3):613-623.

Wilson, B.A. et al. (2003) Prentice Hall Nurse's Drug Guide 2003 Companion Website. [online]. Retrieved from: http://wps.prenhall.com/chet_wilson_drugguides_ 1 /6/1576/403472.cw/index.html; accessed Sep. 30, 2014.

Amalfitano, et al., "Recombinant human acid a-glucosidase enzyme therapy for infantile glycogen storage disease type II: Results of a phase I/II clinical trial", Genetics in Medicine 3(2): 132-138 (2001).

Asano, N, et al., "Nitrogen-in-the-ring pyranoses and furanoses: structural basis of inhibition of mammalian glycosidases", J Med Chem, 37:3701-3706. (1994).

Banati, M, et al., "Enzyme replacement therapy induces T-cell responses in late-onset Pompe disease", Muscle Nerve, 44(5):720-726. (2011).

Barton, N. W., et al., "Replacement Therapy for Inherited Enzyme Deficiency—Macrophage-Targeted Glucocerebrosidase for Gaucher's Disease", N Eng J Med, 324:1464-1470. (1991).

Beck, M., "Alglucosidase alfa: Long term use in the treatment of patients with Pompe disease", Therapeutics and Clinical Risk Management, 5:767-772. (Sep. 2009).

Butters, T. D., et al., "Imino Sugar Inhibitors for Treating the Lysosomal Glycosphingolipidoses", Glycobiology, 15(10):43E-52R. (2005).

Do, H., et al., "ATB200/AT2221 Cleared Accumulated Glycogen and Reversed Cellular Dysfunction to Increase Functional Muscle Strength in Mouse Model of Pompe Disease", Amicus Technologies: Poster from the 13th Annual Lysosomal Disease Network WORLDSymposium, San Diego, CA, Feb. 13-17, 2017; Poster #7 4, Abstract A-348, 1 page. (2017).

Do, H., "Chemical Conjugation of Targeting Peptide to ERTs Improve Receptor Binding and Substrate Clearance in Mouse Models of Disease", Amicus Technologies: Presentation from the 10th Lysosomal Disease Network WORLDSymposium, San Diego, CA, Feb. 10-13, 2014; 14 pages. (Feb. 13, 2014).

Do, H, et al., "Chemical Conjugation of Targeting Peptide to ERTs Improve Receptor Binding and Substrate Clearance in Mouse Models of Disease", Amicus Technologies: Poster from the 10th Annual Lysosomal Disease Network WORLDSymposium, San Diego, CA, Feb. 10-13, 2014, Abstract #277; 1 page. (Feb. 13, 2014).

Gotschall, R., et al., "ATB200/AT2221 Reverses Cellular Dysfunction and Increases Muscle Strength in a Pompe Disease Mouse Model", Amicus Therapeutics: Poster from the 4th International Glycogen Storage Disease (GSD) Conference, Jun. 15-17, 2017, University Medical Center, Groningen, The Netherlands; Abstract 48, 1 page.

Gotschall, R., "Novel rhGAA with Optimal Glycosylation Is Significantly Better than Alglucosidase Alfa for Glycogen Clearance in Skeletal Muscles of Gaa KO Mice", Amicus Technologies: Poster from the ACMG Annual Clinical Genetics Meeting, Mar. 25-27, 2015, Salt Lake City, Utah; Abstract #739, 1 page. (2015).

Gotschall, R., "Novel rhGAA with Optimal Glycosylation Is Significantly Better than Alglucosidase Alfa for Glycogen Clearance in Skeletal Muscles of Gaa KO Mice", Amicus Technologies: Presentation from the 11th Lysosomal Disease Network WorldSymposium, Feb. 9-13, 2015, Orlando, Florida; 12 pages. (2015).

Gotschall, R., et al., "Novel rhGAA with Optimal Glycosylation Is Significantly Better than Alglucosidase Alfa for Glycogen Clearance in Skeletal Muscles of Gaa KO Mice", Amicus Technologies: Abstract from the 11th Lysosomal Disease Network WORLDSymposium, Feb. 9-13, 2015, Orlando, Florida. Abstract 94, 1 page. (2015).

Johnson, F. K., et al., "First-in-Human Preliminary Pharmacokinetic and Safety Data on a Novel Recombinant Acid a-Glucosidase, ATB200, Co-administered With the Pharmacological Chaperone AT2221 in ERT-Experienced Patients With Pompe Disease", Amicus Technologies: Poster from the 13th Annual Lysosomal Disease Network WORLDSymposium, San Diego, CA, Feb. 13-17, 2017; Poster #LB-26, 1 page.

Khanna, R., The pharmacological chaperone AT2220 increases the specific activity and lysosomal delivery of mutant acid alpha-glucosidase, and promotes glycogen reduction in a transgenic mouse model of Pompe disease (2014).

Khanna, R., et al., "Co-Administration of the Pharmacological Chaperone AT2221 with A Proprietary Recombinant Human Acid a-Glucosidase Leads to Greater Plasma Exposure and Substrate Reduction Compared to Alglucosidase Alfa", Amicus Therapeutics: Poster from the 12th Annual Lysosomal Disease Network WORLDSymposium Meeting, Feb. 29-Mar. 4, 2016, San Diego, California; 1 page.

Lembcke, B., et al., "Lysosomal storage of glycogen as a sequel of alpha-glucosidase inhibition by the absorbed deoxynojirimycin derivative emiglitate (BAYo1248). A drug-induced pattern of hepatic glycogen storage mimicking Pompe's disease (glycogenesis type II)", Res Exp Med, 191 (6): 389-404. (1991).

Liu, et al., "The Impact of Sialic Acids on the Pharmacokinetics of a PEGylated Erythropoietin", Journal of Pharmaceutical Sciences, 2012, 101 :4414-4418.

Lun, Y., et al., "A Novel Recombinant Human Acid Alpha-Glucosidase, ATB200, Leads to Greater Substrate Reduction and Improvement in Pompe Disease-Relevant Markers Compared to Alglucosidase Alfa in Gaa KO Mice", Amicus Technologies: Poster from the 13th Annual Lysosomal Disease Network WORLDSymposium, San Diego, CA, Feb. 13-17, 2017; 1 page.

Lun, Y., et al., "Histological examination of the effect of a highly phosphorylated proprietary recombinant human acid alpha-glucosidase on glycogen reduction in disease-relevant muscles of Pompe mice", Amicus Technologies: Poster from the Lysosomal Disease Network 11th WORLDSymposium, Feb. 9-13, 2015, Orlando, Florida; 1 page.

Lun, Y., et al., "Stabilized Next-Generation Recombinant Human Acid Alpha-Glucosidase ATB200 Clears Accumulated Glycogen and Reverses Cellular Dysfunction to Increase Muscle Strength in A Mouse Model of Pompe Disease", Amicus Therapeutics: Poster from the 2017 Muscular Dystrophy Association Scientific Conference, Mar. 19-11, 2017, Arlington, Virginia; 1 page.

Martiniuk, et al., "Correction of Glycogen Storage Disease Type II by Enzyme Replacement with a Recombinant Human Acid Maltase Produced by Over-Expression in a CHO-HDFR"e9 Cell Line, Biochemical and Biophysical Research Communications, 276(3):917-923 (2000).

McVie-Wylie, et al., "Biochemical and pharmacological characterization of different recombinant acid aglucosidase preparations evaluated for the treatment of Pompe disease", Molecular Genetics and Metabolism, 94: 448-455 (2008).

Raben, et al., "Deconstructing Pompe Disease by Analyzing Single Muscle Fibers", Autophagy, 2007, 3, pp. 546-552.

Sathe, S., et al., "Preliminary Pharmacokinetic and Safety Data in Patients With Pompe Disease in Firstin—Human Study Receiving ATB200/AT2221", Amicus Therapeutics: Poster from the 2017 Muscular Dystrophy Association Scientific Conference, Mar. 19-11, 2017, Arlington, Virginia; 1 page.

Sathe, S., et al., "Preliminary Safety, Pharmacokinetic, Pharmacodynamic, and Efficacy Data in Patients With Pompe Disease Receiving ATB200/AT2221 in First-in-Human Study", Amicus Therapeutics: Poster from the 4th International Glycogen

(56) References Cited

OTHER PUBLICATIONS

Storage Disease (GSD) Conference, Jun. 15-17, 2017, University Medical Center, Groningen, The Netherlands; 1 page.

Sola, et al., "Glycosylation of Therapeutic Proteins: An Effective Strategy to Optimize Efficacy", BioDrugs., 2010, 24 (1):9-21.

Stanley, et al., "Essentials of Glycobiology", 2nd edition, Cold Spring Harbor (NY): Cold Spring Harbor Laboratory Press, Chapter 8, NCBI Bookshelf, 10 pages, 2009.

Valenzano, K. J., et al., "Identification and characterization of pharmacological chaperones to correct enzyme deficiencies in lysosomal storage disorders", Assay and Drug Development Technologies, 9(3):213-235. (Jun. 2011).

Van Hove, J.L.K., et al., "High-level production of recombinant human lysosomal acid a-glucosidase in Chinese hamster ovary cells which targets to heart muscle and corrects glycogen accumulation in fibroblasts from patients with Pompe disease", Proc Natl Acad Sci USA, 93:65-70. (1996).

Xu, et al., "Improved efficacy of a next-generation ERT in murine Pompe disease", JCI Insight, 2019, 4(5):e125358, 20 pages.

Zhou, et al., "The Mechanistic Impact of N-Glycosylation on Stability, Pharmacokinetics, and Immunogenicity of Therapeutic Proteins", Journal of Pharmaceutical Sciences, 2019, 108:1366-1377.

Structure and Receptor Affinity for High Mannose and Phosphorylated Oligosaccharides Non-phosphorylated High Mannose N-glycan:

Mono-M6P N-glycan: Lower affinity for CI-MPR ($K_D$ ~ 7000 nM)

Bis-M6P N-glycan: High Affinity for CI-MPR ($K_D$ = 2 nM)

Chemical Structure of Mannose 6-phosphate

Mannose 6-phosphate (M6P)

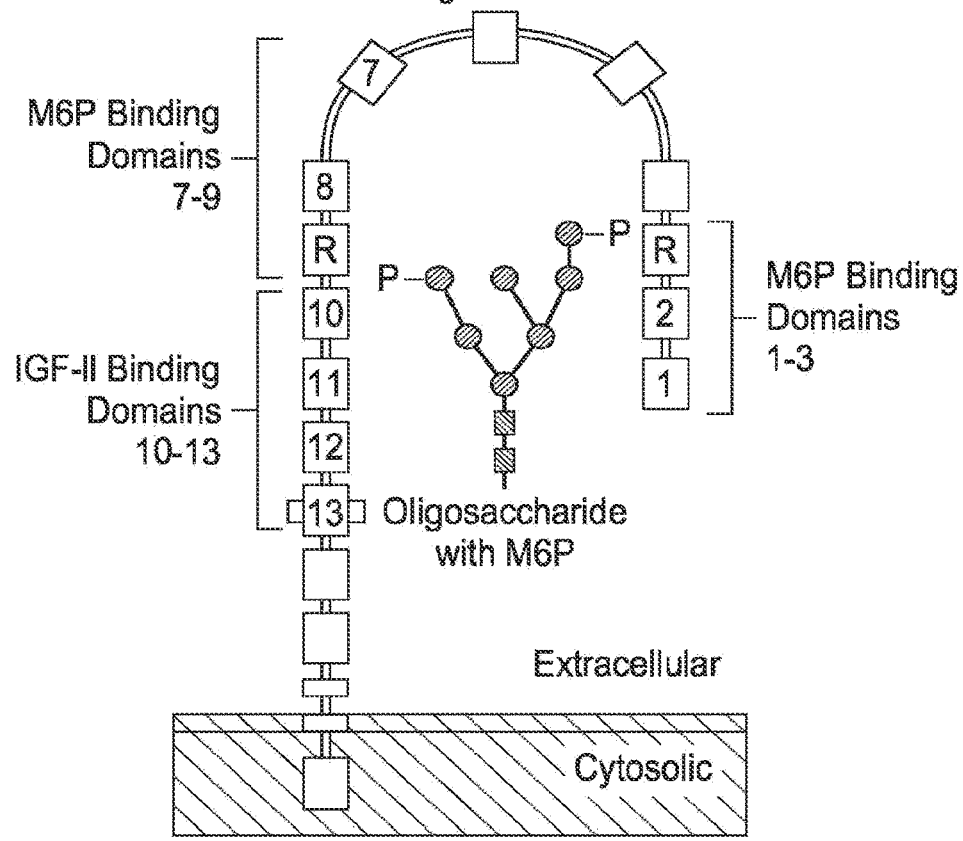

Fig. 3A

Ligands; Affinity and In Vivo Location of Three Glycoprotein Receptors

| Ligand | Receptor | Affinity (nmolar) | Location |
|---|---|---|---|
| Bis-Phosphoylated Glycan | CIMPR | 2 | All Cells |
| Mono-Phosphorylated Glycan | CIMPR | 7,000 | All Cells |
| High Mannose Glycan | Mannose Receptor | 20[b] | Macrophages Dendritic Cells |
| De-sialylated Complex Glycan | Asialyoglycoprotein Receptor | 7[c] | Hepatocytes |

Reference: [a]Tong *et al* 1989; [b]Taylor *et al* 1992; [c]Schwartz *et al* 1981

Fig. 3B

CIMPR Binding Profile of LUMIZYME® compared to that of ATB-200 rhGAA

Distribution of N-Glycans on rhGAA Preparations

| | LUMIZYME® | BP-rhGAA* | ATB200 1 | ATB200 2 |
|---|---|---|---|---|
| Complex Type N-Glycans | 70.7% | 48.9% | 51.0% | 47.5% |
| Hybrid Type N-Glycans | 6.7% | 9.7% | 4.4% | 3.7% |
| High Mannose Type N-Glycans: | | | | |
| Non-phosphorylated | 15.8% | 23.7% | 14.0% | 9.9% |
| Mono-M6P | 5.2% | 10.4% | 13.4% | 14.2% |
| Bis-M6P | 1.6% | 6.8% | 17.2% | 24.7% |

Fig. 9

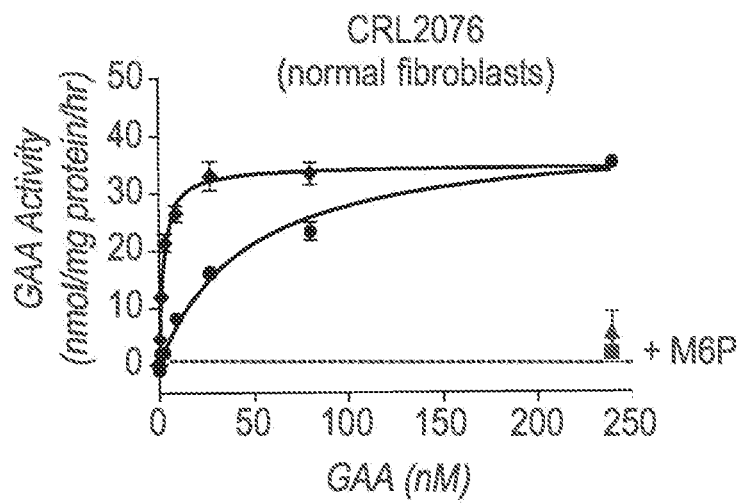
*Fig. 11A*
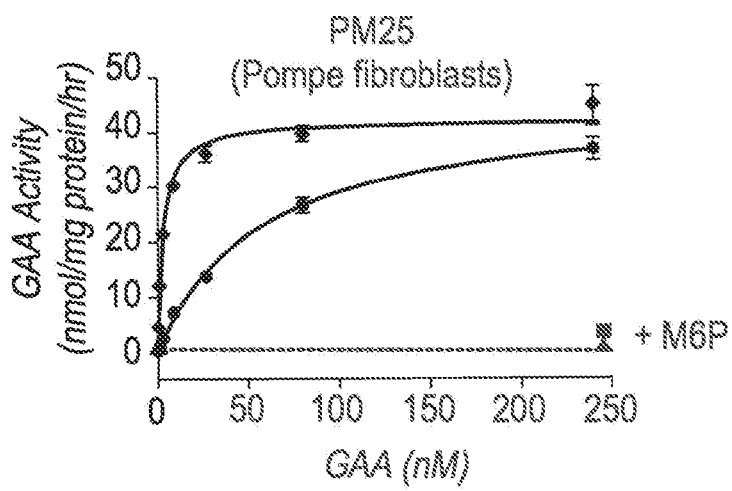
*Fig. 11B*
$K_{uptake}$ Comparison in Normal and Pompe Fibroblasts
| Cell Line | $K_{uptake}$ (nM) | |
|---|---|---|
| | AT200 | LUMIZYME® |
| normal | 2 | 56 |
| Pompe | 3 | 57 |
*Fig. 11C*

Comparative glycogen clearance by ATB-200 rhGAA and LUMIZYME® rhGAA
in Heart, Quadriceps and Tricep muscles Glycogen Reduction in Heart Glycogen Reduction in Quadriceps Summary of Melting Temp of ATB200 with increasing amounts of AT2221

| Buffer | $T_m$ (°C) of ATB200 |
|---|---|
| pH 7.4 | 56.2 |
| pH 7.4 + 10 mM AT2221 | 61.6 |
| pH 7.4 + 30 mM AT2221 | 62.9 |
| pH 7.4 + 100 mM AT2221 | 66.0 |
| pH 5.2 | 67.3 |

| Comparison of % glycogen reduction in *Gaa* KO mice after LUMIZYME® or ATB200 administration (with or without miglustat) | | |
|---|---|---|
| Enzyme ± Chaperone | Quadriceps | Triceps |
| LUMIZYME® alone (20 mg/Kg) | 14 | 14 |
| ATB200 alone (20 mg/kg) | 74 | 62 |
| ATB200 + Miglustat (AT2221) (20 mg/kg) + (10 mg/kg) | 94 | 73 |

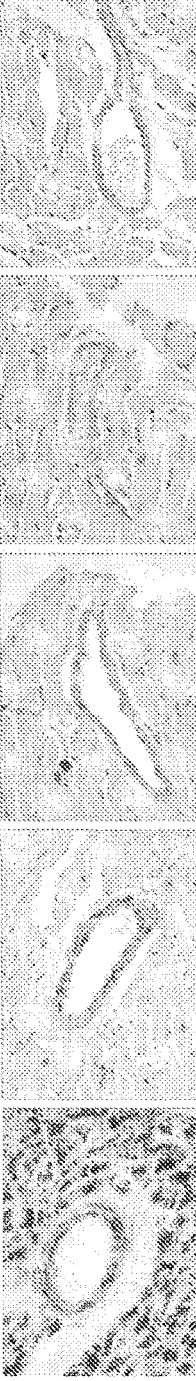
Fig. 17A PAS glycogen staining and EM of Cardiac muscle tissue from GAA KO mice treated with conventional rhGAA or ATB-200 rhGAA and Miglustat (AT-2221)
PAS Staining of Glycogen: vehicle, rhGAA (20mg/kg), ATB200 (20mg/kg), ATB200 (20mg/kg) +Miglustat (10mg/kg), wild type
Fig. 17B Evaluation of Lysosomal Proliferation by LAMP-1 marker
vehicle, rhGAA (20mg/kg), ATB200 (20mg/kg), ATB200 (20mg/kg) +Miglustat (10mg/kg), wild type

SEQUENCE LISTING

```
<160> NUMBER OF SEQ ID NOS: 4

<210> SEQ ID NO 1
<211> LENGTH: 952
<212> TYPE: PRT
<213> ORGANISM: Homo sapiens
<220> FEATURE:
<221> NAME/KEY: SITE
<222> LOCATION: (1)..(952)
<223> OTHER INFORMATION: Sequence 4 from patent US 8592362GenBank:
      AHE24104.1

<400> SEQUENCE: 1

Met Gly Val Arg His Pro Pro Cys Ser His Arg Leu Leu Ala Val Cys
1               5                   10                  15

Ala Leu Val Ser Leu Ala Thr Ala Ala Leu Leu Gly His Ile Leu Leu
            20                  25                  30
```

His Asp Phe Leu Leu Val Pro Arg Glu Leu Ser Gly Ser Ser Pro Val
            35                  40                  45

Leu Glu Glu Thr His Pro Ala His Gln Gln Gly Ala Ser Arg Pro Gly
 50                  55                  60

Pro Arg Asp Ala Gln Ala His Pro Gly Arg Pro Arg Ala Val Pro Thr
 65                  70                  75                  80

Gln Cys Asp Val Pro Pro Asn Ser Arg Phe Asp Cys Ala Pro Asp Lys
                 85                  90                  95

Ala Ile Thr Gln Glu Gln Cys Glu Ala Arg Gly Cys Cys Tyr Ile Pro
             100                 105                 110

Ala Lys Gln Gly Leu Gln Gly Ala Gln Met Gly Gln Pro Trp Cys Phe
         115                 120                 125

Phe Pro Pro Ser Tyr Pro Ser Tyr Lys Leu Glu Asn Leu Ser Ser Ser
130                 135                 140

Glu Met Gly Tyr Thr Ala Thr Leu Thr Arg Thr Thr Pro Thr Phe Phe
145                 150                 155                 160

Pro Lys Asp Ile Leu Thr Leu Arg Leu Asp Val Met Met Glu Thr Glu
                165                 170                 175

Asn Arg Leu His Phe Thr Ile Lys Asp Pro Ala Asn Arg Arg Tyr Glu
            180                 185                 190

Val Pro Leu Glu Thr Pro Arg Val His Ser Arg Ala Pro Ser Pro Leu
        195                 200                 205

Tyr Ser Val Glu Phe Ser Glu Glu Pro Phe Gly Val Ile Val His Arg
    210                 215                 220

Gln Leu Asp Gly Arg Val Leu Leu Asn Thr Thr Val Ala Pro Leu Phe
225                 230                 235                 240

Phe Ala Asp Gln Phe Leu Gln Leu Ser Thr Ser Leu Pro Ser Gln Tyr
                245                 250                 255

Ile Thr Gly Leu Ala Glu His Leu Ser Pro Leu Met Leu Ser Thr Ser
            260                 265                 270

Trp Thr Arg Ile Thr Leu Trp Asn Arg Asp Leu Ala Pro Thr Pro Gly
        275                 280                 285

Ala Asn Leu Tyr Gly Ser His Pro Phe Tyr Leu Ala Leu Glu Asp Gly
    290                 295                 300

Gly Ser Ala His Gly Val Phe Leu Leu Asn Ser Asn Ala Met Asp Val
305                 310                 315                 320

Val Leu Gln Pro Ser Pro Ala Leu Ser Trp Arg Ser Thr Gly Gly Ile
                325                 330                 335

Leu Asp Val Tyr Ile Phe Leu Gly Pro Glu Pro Lys Ser Val Val Gln
            340                 345                 350

Gln Tyr Leu Asp Val Val Gly Tyr Pro Phe Met Pro Pro Tyr Trp Gly
        355                 360                 365

Leu Gly Phe His Leu Cys Arg Trp Gly Tyr Ser Ser Thr Ala Ile Thr
    370                 375                 380

Arg Gln Val Val Glu Asn Met Thr Arg Ala His Phe Pro Leu Asp Val
385                 390                 395                 400

Gln Trp Asn Asp Leu Asp Tyr Met Asp Ser Arg Arg Asp Phe Thr Phe
                405                 410                 415

Asn Lys Asp Gly Phe Arg Asp Phe Pro Ala Met Val Gln Glu Leu His
            420                 425                 430

Gln Gly Gly Arg Arg Tyr Met Met Ile Val Asp Pro Ala Ile Ser Ser
        435                 440                 445

```
-continued

Ser Gly Pro Ala Gly Ser Tyr Arg Pro Tyr Asp Glu Gly Leu Arg Arg
    450                 455                 460

Gly Val Phe Ile Thr Asn Glu Thr Gly Gln Pro Leu Ile Gly Lys Val
465                 470                 475                 480

Trp Pro Gly Ser Thr Ala Phe Pro Asp Phe Thr Asn Pro Thr Ala Leu
            485                 490                 495

Ala Trp Trp Glu Asp Met Val Ala Glu Phe His Asp Gln Val Pro Phe
        500                 505                 510

Asp Gly Met Trp Ile Asp Met Asn Glu Pro Ser Asn Phe Ile Arg Gly
            515                 520                 525

Ser Glu Asp Gly Cys Pro Asn Asn Glu Leu Glu Asn Pro Pro Tyr Val
530                 535                 540

Pro Gly Val Val Gly Gly Thr Leu Gln Ala Ala Thr Ile Cys Ala Ser
545                 550                 555                 560

Ser His Gln Phe Leu Ser Thr His Tyr Asn Leu His Asn Leu Tyr Gly
                565                 570                 575

Leu Thr Glu Ala Ile Ala Ser His Arg Ala Leu Val Lys Ala Arg Gly
            580                 585                 590

Thr Arg Pro Phe Val Ile Ser Arg Ser Thr Phe Ala Gly His Gly Arg
        595                 600                 605

Tyr Ala Gly His Trp Thr Gly Asp Val Trp Ser Ser Trp Glu Gln Leu
    610                 615                 620

Ala Ser Ser Val Pro Glu Ile Leu Gln Phe Asn Leu Leu Gly Val Pro
625                 630                 635                 640

Leu Val Gly Ala Asp Val Cys Gly Phe Leu Gly Asn Thr Ser Glu Glu
                645                 650                 655

Leu Cys Val Arg Trp Thr Gln Leu Gly Ala Phe Tyr Pro Phe Met Arg
            660                 665                 670

Asn His Asn Ser Leu Leu Ser Leu Pro Gln Glu Pro Tyr Ser Phe Ser
        675                 680                 685

Glu Pro Ala Gln Gln Ala Met Arg Lys Ala Leu Thr Leu Arg Tyr Ala
    690                 695                 700

Leu Leu Pro His Leu Tyr Thr Leu Phe His Gln Ala His Val Ala Gly
705                 710                 715                 720

Glu Thr Val Ala Arg Pro Leu Phe Leu Glu Phe Pro Lys Asp Ser Ser
                725                 730                 735

Thr Trp Thr Val Asp His Gln Leu Leu Trp Gly Glu Ala Leu Leu Ile
            740                 745                 750

Thr Pro Val Leu Gln Ala Gly Lys Ala Glu Val Thr Gly Tyr Phe Pro
        755                 760                 765

Leu Gly Thr Trp Tyr Asp Leu Gln Thr Val Pro Ile Glu Ala Leu Gly
    770                 775                 780

Ser Leu Pro Pro Pro Ala Ala Pro Arg Glu Pro Ala Ile His Ser
785                 790                 795                 800

Glu Gly Gln Trp Val Thr Leu Pro Ala Pro Leu Asp Thr Ile Asn Val
                805                 810                 815

His Leu Arg Ala Gly Tyr Ile Ile Pro Leu Gln Gly Pro Gly Leu Thr
            820                 825                 830

Thr Thr Glu Ser Arg Gln Gln Pro Met Ala Leu Ala Val Ala Leu Thr
        835                 840                 845

Lys Gly Gly Glu Ala Arg Gly Glu Leu Phe Trp Asp Asp Gly Glu Ser
    850                 855                 860

Leu Glu Val Leu Glu Arg Gly Ala Tyr Thr Gln Val Ile Phe Leu Ala
```

```
                865                 870                 875                 880
Arg Asn Asn Thr Ile Val Asn Glu Leu Val Arg Val Thr Ser Glu Gly
                    885                 890                 895

Ala Gly Leu Gln Leu Gln Lys Val Thr Val Leu Gly Val Ala Thr Ala
                900                 905                 910

Pro Gln Val Leu Ser Asn Gly Val Pro Val Ser Asn Phe Thr Tyr
            915                 920                 925

Ser Pro Asp Thr Lys Val Leu Asp Ile Cys Val Ser Leu Leu Met Gly
        930                 935                 940

Glu Gln Phe Leu Val Ser Trp Cys
945                 950

<210> SEQ ID NO 2
<211> LENGTH: 3624
<212> TYPE: DNA
<213> ORGANISM: Homo sapiens
<220> FEATURE:
<221> NAME/KEY: CDS
<222> LOCATION: (220)..(3078)
<223> OTHER INFORMATION: H.sapiens GAA mRNA for lysosomal alpha-
      glucosidase (acid maltase); GenBank: Y00839.1

<400> SEQUENCE: 2
cagttgggaa agctgaggtt gtcgccgggg ccgcgggtgg aggtcgggga tgaggcagca      60
ggtaggacag tgacctcggt gacgcgaagg accccggcca cctctaggtt ctcctcgtcc     120
gcccgttgtt cagcgaggga ggctctgggc ctgccgcagc tgacggggaa actgaggcac     180
ggagcgggcc tgtaggagct gtccaggcca tctccaacc atg gga gtg agg cac       234
                                            Met Gly Val Arg His
                                              1               5 ccg ccc tgc tcc cac cgg ctc ctg gcc gtc tgc gcc ctc gtg tcc ttg       282
Pro Pro Cys Ser His Arg Leu Leu Ala Val Cys Ala Leu Val Ser Leu
                10                  15                  20 gca acc gct gca ctc ctg ggg cac atc cta ctc cat gat ttc ctg ctg       330
Ala Thr Ala Ala Leu Leu Gly His Ile Leu Leu His Asp Phe Leu Leu
            25                  30                  35 gtt ccc cga gag ctg agt ggc tcc tcc cca gtc ctg gag gag act cac       378
Val Pro Arg Glu Leu Ser Gly Ser Ser Pro Val Leu Glu Glu Thr His
        40                  45                  50 cca gct cac cag cag gga gcc agc aga cca ggg ccc cgg gat gcc cag       426
Pro Ala His Gln Gln Gly Ala Ser Arg Pro Gly Pro Arg Asp Ala Gln
    55                  60                  65 gca cac ccc ggc cgt ccc aga gca gtg ccc aca cag tgc gac gtc ccc       474
Ala His Pro Gly Arg Pro Arg Ala Val Pro Thr Gln Cys Asp Val Pro
70                  75                  80                  85 ccc aac agc cgc ttc gat tgc gcc cct gac aag gcc atc acc cag gaa       522
Pro Asn Ser Arg Phe Asp Cys Ala Pro Asp Lys Ala Ile Thr Gln Glu
                90                  95                 100 cag tgc gag gcc cgc ggc tgc tgc tac atc cct gca aag cag ggg ctg       570
Gln Cys Glu Ala Arg Gly Cys Cys Tyr Ile Pro Ala Lys Gln Gly Leu
            105                 110                 115 cag gga gcc cag atg ggg cag ccc tgg tgc ttc ttc cca ccc agc tac       618
Gln Gly Ala Gln Met Gly Gln Pro Trp Cys Phe Phe Pro Pro Ser Tyr
        120                 125                 130 ccc agc tac aag ctg gag aac ctg agc tcc tct gaa atg ggc tac acg       666
Pro Ser Tyr Lys Leu Glu Asn Leu Ser Ser Ser Glu Met Gly Tyr Thr
    135                 140                 145 gcc acc ctg acc cgt acc acc ccc acc ttc ttc ccc aag gac atc ctg       714
Ala Thr Leu Thr Arg Thr Thr Pro Thr Phe Phe Pro Lys Asp Ile Leu
150                 155                 160                 165
```

| | | |
|---|---|---|
| acc ctg cgg ctg gac gtg atg atg gag act gag aac cgc ctc cac ttc<br>Thr Leu Arg Leu Asp Val Met Met Glu Thr Glu Asn Arg Leu His Phe<br>170 175 180 | 762 | |
| acg atc aaa gat cca gct aac agg cgc tac gag gtg ccc ttg gag acc<br>Thr Ile Lys Asp Pro Ala Asn Arg Arg Tyr Glu Val Pro Leu Glu Thr<br>185 190 195 | 810 | |
| ccg cgt gtc cac agc cgg gca ccg tcc cca ctc tac agc gtg gag ttc<br>Pro Arg Val His Ser Arg Ala Pro Ser Pro Leu Tyr Ser Val Glu Phe<br>200 205 210 | 858 | |
| tcc gag gag ccc ttc ggg gtg atc gtg cac cgg cag ctg gac ggc cgc<br>Ser Glu Glu Pro Phe Gly Val Ile Val His Arg Gln Leu Asp Gly Arg<br>215 220 225 | 906 | |
| gtg ctg ctg aac acg acg gtg gcg ccc ctg ttc ttt gcg gac cag ttc<br>Val Leu Leu Asn Thr Thr Val Ala Pro Leu Phe Phe Ala Asp Gln Phe<br>230 235 240 245 | 954 | |
| ctt cag ctg tcc acc tcg ctg ccc tcg cag tat atc aca ggc ctc gcc<br>Leu Gln Leu Ser Thr Ser Leu Pro Ser Gln Tyr Ile Thr Gly Leu Ala<br>250 255 260 | 1002 | |
| gag cac ctc agt ccc ctg atg ctc agc acc agc tgg acc agg atc acc<br>Glu His Leu Ser Pro Leu Met Leu Ser Thr Ser Trp Thr Arg Ile Thr<br>265 270 275 | 1050 | |
| ctg tgg aac cgg gac ctt gcg ccc acg ccc ggt gcg aac ctc tac ggg<br>Leu Trp Asn Arg Asp Leu Ala Pro Thr Pro Gly Ala Asn Leu Tyr Gly<br>280 285 290 | 1098 | |
| tct cac cct ttc tac ctg gcg ctg gag gac ggc ggg tcg gca cac ggg<br>Ser His Pro Phe Tyr Leu Ala Leu Glu Asp Gly Gly Ser Ala His Gly<br>295 300 305 | 1146 | |
| gtg ttc ctg cta aac agc aat gcc atg gat gtg gtc ctg cag ccg agc<br>Val Phe Leu Leu Asn Ser Asn Ala Met Asp Val Val Leu Gln Pro Ser<br>310 315 320 325 | 1194 | |
| cct gcc ctt agc tgg agg tcg aca ggt ggg atc ctg gat gtc tac atc<br>Pro Ala Leu Ser Trp Arg Ser Thr Gly Gly Ile Leu Asp Val Tyr Ile<br>330 335 340 | 1242 | |
| ttc ctg ggc cca gag ccc aag agc gtg gtg cag cag tac ctg gac gtt<br>Phe Leu Gly Pro Glu Pro Lys Ser Val Val Gln Gln Tyr Leu Asp Val<br>345 350 355 | 1290 | |
| gtg gga tac ccg ttc atg ccg cca tac tgg ggc ctg ggc ttc cac ctg<br>Val Gly Tyr Pro Phe Met Pro Pro Tyr Trp Gly Leu Gly Phe His Leu<br>360 365 370 | 1338 | |
| tgc cgc tgg ggc tac tcc tcc acc gct atc acc cgc cag gtg gtg gag<br>Cys Arg Trp Gly Tyr Ser Ser Thr Ala Ile Thr Arg Gln Val Val Glu<br>375 380 385 | 1386 | |
| aac atg acc agg gcc cac ttc ccc ctg gac gtc caa tgg aac gac ctg<br>Asn Met Thr Arg Ala His Phe Pro Leu Asp Val Gln Trp Asn Asp Leu<br>390 395 400 405 | 1434 | |
| gac tac atg gac tcc cgg agg gac ttc acg ttc aac aag gat ggc ttc<br>Asp Tyr Met Asp Ser Arg Arg Asp Phe Thr Phe Asn Lys Asp Gly Phe<br>410 415 420 | 1482 | |
| cgg gac ttc ccg gcc atg gtg cag gag ctg cac cag ggc ggc cgg cgc<br>Arg Asp Phe Pro Ala Met Val Gln Glu Leu His Gln Gly Gly Arg Arg<br>425 430 435 | 1530 | |
| tac atg atg atc gtg gat cct gcc atc agc agc tcg ggc cct gcc ggg<br>Tyr Met Met Ile Val Asp Pro Ala Ile Ser Ser Ser Gly Pro Ala Gly<br>440 445 450 | 1578 | |
| agc tac agg ccc tac gac gag ggt ctg cgg agg ggg gtt ttc atc acc<br>Ser Tyr Arg Pro Tyr Asp Glu Gly Leu Arg Arg Gly Val Phe Ile Thr<br>455 460 465 | 1626 | |
| aac gag acc ggc cag ccg ctg att ggg aag gta tgg ccc ggg tcc act<br>Asn Glu Thr Gly Gln Pro Leu Ile Gly Lys Val Trp Pro Gly Ser Thr | 1674 | |

-continued

| | | | |
|---|---|---|---|
| 470 | 475 | 480 | 485 |

```
gcc ttc ccc gac ttc acc aac ccc aca gcc ctg gcc tgg tgg gag gac   1722
Ala Phe Pro Asp Phe Thr Asn Pro Thr Ala Leu Ala Trp Trp Glu Asp
            490                 495                 500 atg gtg gct gag ttc cat gac cag gtg ccc ttc gac ggc atg tgg att   1770
Met Val Ala Glu Phe His Asp Gln Val Pro Phe Asp Gly Met Trp Ile
        505                 510                 515 gac atg aac gag cct tcc aac ttc atc aga ggc tct gag gac ggc tgc   1818
Asp Met Asn Glu Pro Ser Asn Phe Ile Arg Gly Ser Glu Asp Gly Cys
    520                 525                 530 ccc aac aat gag ctg gag aac cca ccc tac gtg cct ggg gtg gtt ggg   1866
Pro Asn Asn Glu Leu Glu Asn Pro Pro Tyr Val Pro Gly Val Val Gly
535                 540                 545 ggg acc ctc cag gcg gcc acc atc tgt gcc tcc agc cac cag ttt ctc   1914
Gly Thr Leu Gln Ala Ala Thr Ile Cys Ala Ser Ser His Gln Phe Leu
550                 555                 560                 565 tcc aca cac tac aac ctg cac aac ctc tac ggc ctg acc gaa gcc atc   1962
Ser Thr His Tyr Asn Leu His Asn Leu Tyr Gly Leu Thr Glu Ala Ile
            570                 575                 580 gcc tcc cac agg gcg ctg gtg aag gct cgg ggg aca cgc cca ttt gtg   2010
Ala Ser His Arg Ala Leu Val Lys Ala Arg Gly Thr Arg Pro Phe Val
        585                 590                 595 atc tcc cgc tcg acc ttt gct ggc cac ggc cga tac gcc ggc cac tgg   2058
Ile Ser Arg Ser Thr Phe Ala Gly His Gly Arg Tyr Ala Gly His Trp
    600                 605                 610 acg ggg gac gtg tgg agc tcc tgg gag cag ctc gcc tcc tcc gtg cca   2106
Thr Gly Asp Val Trp Ser Ser Trp Glu Gln Leu Ala Ser Ser Val Pro
615                 620                 625 gaa atc ctg cag ttt aac ctg ctg ggg gtg cct ctg gtc ggg gcc gac   2154
Glu Ile Leu Gln Phe Asn Leu Leu Gly Val Pro Leu Val Gly Ala Asp
630                 635                 640                 645 gtc tgc ggc ttc ctg ggc aac acc tca gag gag ctg tgt gtg cgc tgg   2202
Val Cys Gly Phe Leu Gly Asn Thr Ser Glu Glu Leu Cys Val Arg Trp
            650                 655                 660 acc cag ctg ggg gcc ttc tac ccc ttc atg cgg aac cac aac agc ctg   2250
Thr Gln Leu Gly Ala Phe Tyr Pro Phe Met Arg Asn His Asn Ser Leu
        665                 670                 675 ctc agt ctg ccc cag gag ccg tac agc ttc agc gag ccg gcc cag cag   2298
Leu Ser Leu Pro Gln Glu Pro Tyr Ser Phe Ser Glu Pro Ala Gln Gln
    680                 685                 690 gcc atg agg aag gcc ctc acc ctg cgc tac gca ctc ctc ccc cac ctc   2346
Ala Met Arg Lys Ala Leu Thr Leu Arg Tyr Ala Leu Leu Pro His Leu
695                 700                 705 tac aca ctg ttc cac cag gcc cac gtc gcg ggg gag acc gtg gcc cgg   2394
Tyr Thr Leu Phe His Gln Ala His Val Ala Gly Glu Thr Val Ala Arg
710                 715                 720                 725 ccc ctc ttc ctg gag ttc ccc aag gac tct agc acc tgg act gtg gac   2442
Pro Leu Phe Leu Glu Phe Pro Lys Asp Ser Ser Thr Trp Thr Val Asp
            730                 735                 740 cac cag ctc ctg tgg ggg gag gcc ctg ctc atc acc cca gtg ctc cag   2490
His Gln Leu Leu Trp Gly Glu Ala Leu Leu Ile Thr Pro Val Leu Gln
        745                 750                 755 gcc ggg aag gcc gaa gtg act ggc tac ttc ccc ttg ggc aca tgg tac   2538
Ala Gly Lys Ala Glu Val Thr Gly Tyr Phe Pro Leu Gly Thr Trp Tyr
    760                 765                 770 gac ctg cag acg gtg cca ata gag gcc ctt ggc agc ctc cca ccc cca   2586
Asp Leu Gln Thr Val Pro Ile Glu Ala Leu Gly Ser Leu Pro Pro Pro
775                 780                 785 cct gca gct ccc cgt gag cca gcc atc cac agc gag ggg cag tgg gtg   2634
```

```
Pro Ala Ala Pro Arg Glu Pro Ala Ile His Ser Glu Gly Gln Trp Val
790                 795                 800                 805 acg ctg ccg gcc ccc ctg gac acc atc aac gtc cac ctc cgg gct ggg    2682
Thr Leu Pro Ala Pro Leu Asp Thr Ile Asn Val His Leu Arg Ala Gly
                810                 815                 820 tac atc atc ccc ctg cag ggc cct ggc ctc aca acc aca gag tcc cgc    2730
Tyr Ile Ile Pro Leu Gln Gly Pro Gly Leu Thr Thr Thr Glu Ser Arg
            825                 830                 835 cag cag ccc atg gcc ctg gct gtg gcc ctg acc aag ggt gga gag gcc    2778
Gln Gln Pro Met Ala Leu Ala Val Ala Leu Thr Lys Gly Gly Glu Ala
        840                 845                 850 cga ggg gag ctg ttc tgg gac gat gga gag agc ctg gaa gtg ctg gag    2826
Arg Gly Glu Leu Phe Trp Asp Asp Gly Glu Ser Leu Glu Val Leu Glu
    855                 860                 865 cga ggg gcc tac aca cag gtc atc ttc ctg gcc agg aat aac acg atc    2874
Arg Gly Ala Tyr Thr Gln Val Ile Phe Leu Ala Arg Asn Asn Thr Ile
870                 875                 880                 885 gtg aat gag ctg gta cgt gtg acc agt gag gga gct ggc ctg cag ctg    2922
Val Asn Glu Leu Val Arg Val Thr Ser Glu Gly Ala Gly Leu Gln Leu
                890                 895                 900 cag aag gtg act gtc ctg ggc gtg gcc acg gcg ccc cag cag gtc ctc    2970
Gln Lys Val Thr Val Leu Gly Val Ala Thr Ala Pro Gln Gln Val Leu
            905                 910                 915 tcc aac ggt gtc cct gtc tcc aac ttc acc tac agc ccc gac acc aag    3018
Ser Asn Gly Val Pro Val Ser Asn Phe Thr Tyr Ser Pro Asp Thr Lys
        920                 925                 930 gtc ctg gac atc tgt gtc tcg ctg ttg atg gga gag cag ttt ctc gtc    3066
Val Leu Asp Ile Cys Val Ser Leu Leu Met Gly Glu Gln Phe Leu Val
    935                 940                 945 agc tgg tgt tag ccgggcggag tgtgttagtc tctccagagg gaggctggtt        3118
Ser Trp Cys
950 ccccagggaa gcagagcctg tgtgcgggca gcagctgtgt gcgggcctgg gggttgcatg  3178 tgtcacctgg agctgggcac taaccattcc aagccgccgc atcgcttgtt tccacctcct  3238 gggccgggc tctggcccc aacgtgtcta ggagagcttt ctccctagat cgcactgtgg    3298 gccgggcct ggagggctgc tctgtgttaa taagattgta aggtttgccc tcctcacctg    3358 ttgccggcat gcgggtagta ttagccaccc ccctccatct gttcccagca ccggagaagg  3418 gggtgctcag gtggaggtgt ggggtatgca cctgagctcc tgcttcgcgc ctgctgctct  3478 gccccaacgc gaccgcttcc cggctgccca gagggctgga tgcctgccgg tccccgagca  3538 agcctgggaa ctcaggaaaa ttcacaggac ttgggagatt ctaaatctta agtgcaatta  3598 ttttaataaa agggcattt ggaatc                                        3624

<210> SEQ ID NO 3
<211> LENGTH: 952
<212> TYPE: PRT
<213> ORGANISM: Homo sapiens

<400> SEQUENCE: 3

Met Gly Val Arg His Pro Pro Cys Ser His Arg Leu Leu Ala Val Cys
1               5                   10                  15

Ala Leu Val Ser Leu Ala Thr Ala Ala Leu Leu Gly His Ile Leu Leu
            20                  25                  30

His Asp Phe Leu Leu Val Pro Arg Glu Leu Ser Gly Ser Ser Pro Val
        35                  40                  45

Leu Glu Glu Thr His Pro Ala His Gln Gln Gly Ala Ser Arg Pro Gly
```

```
                50                  55                  60
Pro Arg Asp Ala Gln Ala His Pro Gly Arg Pro Arg Ala Val Pro Thr
65                  70                  75                  80

Gln Cys Asp Val Pro Pro Asn Ser Arg Phe Asp Cys Ala Pro Asp Lys
                85                  90                  95

Ala Ile Thr Gln Glu Gln Cys Glu Ala Arg Gly Cys Cys Tyr Ile Pro
                100                 105                 110

Ala Lys Gln Gly Leu Gln Gly Ala Gln Met Gly Gln Pro Trp Cys Phe
                115                 120                 125

Phe Pro Pro Ser Tyr Pro Ser Tyr Lys Leu Glu Asn Leu Ser Ser Ser
                130                 135                 140

Glu Met Gly Tyr Thr Ala Thr Leu Thr Arg Thr Thr Pro Thr Phe Phe
145                 150                 155                 160

Pro Lys Asp Ile Leu Thr Leu Arg Leu Asp Val Met Met Glu Thr Glu
                165                 170                 175

Asn Arg Leu His Phe Thr Ile Lys Asp Pro Ala Asn Arg Arg Tyr Glu
                180                 185                 190

Val Pro Leu Glu Thr Pro Arg Val His Ser Arg Ala Pro Ser Pro Leu
                195                 200                 205

Tyr Ser Val Glu Phe Ser Glu Glu Pro Phe Gly Val Ile Val His Arg
210                 215                 220

Gln Leu Asp Gly Arg Val Leu Leu Asn Thr Thr Val Ala Pro Leu Phe
225                 230                 235                 240

Phe Ala Asp Gln Phe Leu Gln Leu Ser Thr Ser Leu Pro Ser Gln Tyr
                245                 250                 255

Ile Thr Gly Leu Ala Glu His Leu Ser Pro Leu Met Leu Ser Thr Ser
                260                 265                 270

Trp Thr Arg Ile Thr Leu Trp Asn Arg Asp Leu Ala Pro Thr Pro Gly
                275                 280                 285

Ala Asn Leu Tyr Gly Ser His Pro Phe Tyr Leu Ala Leu Glu Asp Gly
                290                 295                 300

Gly Ser Ala His Gly Val Phe Leu Leu Asn Ser Asn Ala Met Asp Val
305                 310                 315                 320

Val Leu Gln Pro Ser Pro Ala Leu Ser Trp Arg Ser Thr Gly Gly Ile
                325                 330                 335

Leu Asp Val Tyr Ile Phe Leu Gly Pro Glu Pro Lys Ser Val Val Gln
                340                 345                 350

Gln Tyr Leu Asp Val Val Gly Tyr Pro Phe Met Pro Pro Tyr Trp Gly
                355                 360                 365

Leu Gly Phe His Leu Cys Arg Trp Gly Tyr Ser Ser Thr Ala Ile Thr
370                 375                 380

Arg Gln Val Val Glu Asn Met Thr Arg Ala His Phe Pro Leu Asp Val
385                 390                 395                 400

Gln Trp Asn Asp Leu Asp Tyr Met Asp Ser Arg Arg Asp Phe Thr Phe
                405                 410                 415

Asn Lys Asp Gly Phe Arg Asp Phe Pro Ala Met Val Gln Glu Leu His
                420                 425                 430

Gln Gly Gly Arg Arg Tyr Met Met Ile Val Asp Pro Ala Ile Ser Ser
                435                 440                 445

Ser Gly Pro Ala Gly Ser Tyr Arg Pro Tyr Asp Glu Gly Leu Arg Arg
                450                 455                 460

Gly Val Phe Ile Thr Asn Glu Thr Gly Gln Pro Leu Ile Gly Lys Val
465                 470                 475                 480
```

-continued

```
Trp Pro Gly Ser Thr Ala Phe Pro Asp Phe Thr Asn Pro Thr Ala Leu
                485                 490                 495

Ala Trp Trp Glu Asp Met Val Ala Glu Phe His Asp Gln Val Pro Phe
            500                 505                 510

Asp Gly Met Trp Ile Asp Met Asn Glu Pro Ser Asn Phe Ile Arg Gly
        515                 520                 525

Ser Glu Asp Gly Cys Pro Asn Asn Glu Leu Glu Asn Pro Pro Tyr Val
    530                 535                 540

Pro Gly Val Val Gly Gly Thr Leu Gln Ala Ala Thr Ile Cys Ala Ser
545                 550                 555                 560

Ser His Gln Phe Leu Ser Thr His Tyr Asn Leu His Asn Leu Tyr Gly
                565                 570                 575

Leu Thr Glu Ala Ile Ala Ser His Arg Ala Leu Val Lys Ala Arg Gly
            580                 585                 590

Thr Arg Pro Phe Val Ile Ser Arg Ser Thr Phe Ala Gly His Gly Arg
        595                 600                 605

Tyr Ala Gly His Trp Thr Gly Asp Val Trp Ser Ser Trp Glu Gln Leu
    610                 615                 620

Ala Ser Ser Val Pro Glu Ile Leu Gln Phe Asn Leu Leu Gly Val Pro
625                 630                 635                 640

Leu Val Gly Ala Asp Val Cys Gly Phe Leu Gly Asn Thr Ser Glu Glu
                645                 650                 655

Leu Cys Val Arg Trp Thr Gln Leu Gly Ala Phe Tyr Pro Phe Met Arg
            660                 665                 670

Asn His Asn Ser Leu Leu Ser Leu Pro Gln Glu Pro Tyr Ser Phe Ser
        675                 680                 685

Glu Pro Ala Gln Gln Ala Met Arg Lys Ala Leu Thr Leu Arg Tyr Ala
    690                 695                 700

Leu Leu Pro His Leu Tyr Thr Leu Phe His Gln Ala His Val Ala Gly
705                 710                 715                 720

Glu Thr Val Ala Arg Pro Leu Phe Leu Glu Phe Pro Lys Asp Ser Ser
                725                 730                 735

Thr Trp Thr Val Asp His Gln Leu Leu Trp Gly Glu Ala Leu Leu Ile
            740                 745                 750

Thr Pro Val Leu Gln Ala Gly Lys Ala Glu Val Thr Gly Tyr Phe Pro
        755                 760                 765

Leu Gly Thr Trp Tyr Asp Leu Gln Thr Val Pro Ile Glu Ala Leu Gly
    770                 775                 780

Ser Leu Pro Pro Pro Ala Ala Pro Arg Glu Pro Ala Ile His Ser
785                 790                 795                 800

Glu Gly Gln Trp Val Thr Leu Pro Ala Pro Leu Asp Thr Ile Asn Val
                805                 810                 815

His Leu Arg Ala Gly Tyr Ile Ile Pro Leu Gln Gly Pro Gly Leu Thr
            820                 825                 830

Thr Thr Glu Ser Arg Gln Gln Pro Met Ala Leu Ala Val Ala Leu Thr
        835                 840                 845

Lys Gly Gly Glu Ala Arg Gly Glu Leu Phe Trp Asp Asp Gly Glu Ser
    850                 855                 860

Leu Glu Val Leu Glu Arg Gly Ala Tyr Thr Gln Val Ile Phe Leu Ala
865                 870                 875                 880

Arg Asn Asn Thr Ile Val Asn Glu Leu Val Arg Val Thr Ser Glu Gly
                885                 890                 895
```

```
Ala Gly Leu Gln Leu Gln Lys Val Thr Val Leu Gly Val Ala Thr Ala
            900                 905                 910

Pro Gln Gln Val Leu Ser Asn Gly Val Pro Val Ser Asn Phe Thr Tyr
            915                 920                 925

Ser Pro Asp Thr Lys Val Leu Asp Ile Cys Val Ser Leu Leu Met Gly
            930                 935                 940

Glu Gln Phe Leu Val Ser Trp Cys
945                 950

<210> SEQ ID NO 4
<211> LENGTH: 952
<212> TYPE: PRT
<213> ORGANISM: Homo sapiens
<220> FEATURE:
<221> NAME/KEY: SITE
<222> LOCATION: (1)..(952)
<223> OTHER INFORMATION: Lysosomal alpha-glucosidase preproprotein [Homo
      sapiens]; NCBI Reference Sequence: NP_000143.2

<400> SEQUENCE: 4

Met Gly Val Arg His Pro Pro Cys Ser His Arg Leu Leu Ala Val Cys
1               5                   10                  15

Ala Leu Val Ser Leu Ala Thr Ala Ala Leu Leu Gly His Ile Leu Leu
            20                  25                  30

His Asp Phe Leu Leu Val Pro Arg Glu Leu Ser Gly Ser Ser Pro Val
        35                  40                  45

Leu Glu Glu Thr His Pro Ala His Gln Gln Gly Ala Ser Arg Pro Gly
    50                  55                  60

Pro Arg Asp Ala Gln Ala His Pro Gly Arg Pro Arg Ala Val Pro Thr
65                  70                  75                  80

Gln Cys Asp Val Pro Pro Asn Ser Arg Phe Asp Cys Ala Pro Asp Lys
                85                  90                  95

Ala Ile Thr Gln Glu Gln Cys Glu Ala Arg Gly Cys Cys Tyr Ile Pro
            100                 105                 110

Ala Lys Gln Gly Leu Gln Gly Ala Gln Met Gly Gln Pro Trp Cys Phe
        115                 120                 125

Phe Pro Pro Ser Tyr Pro Ser Tyr Lys Leu Glu Asn Leu Ser Ser Ser
    130                 135                 140

Glu Met Gly Tyr Thr Ala Thr Leu Thr Arg Thr Thr Pro Thr Phe Phe
145                 150                 155                 160

Pro Lys Asp Ile Leu Thr Leu Arg Leu Asp Val Met Met Glu Thr Glu
                165                 170                 175

Asn Arg Leu His Phe Thr Ile Lys Asp Pro Ala Asn Arg Arg Tyr Glu
            180                 185                 190

Val Pro Leu Glu Thr Pro His Val His Ser Arg Ala Pro Ser Pro Leu
        195                 200                 205

Tyr Ser Val Glu Phe Ser Glu Glu Pro Phe Gly Val Ile Val Arg Arg
    210                 215                 220

Gln Leu Asp Gly Arg Val Leu Leu Asn Thr Thr Val Ala Pro Leu Phe
225                 230                 235                 240

Phe Ala Asp Gln Phe Leu Gln Leu Ser Thr Ser Leu Pro Ser Gln Tyr
                245                 250                 255

Ile Thr Gly Leu Ala Glu His Leu Ser Pro Leu Met Leu Ser Thr Ser
            260                 265                 270

Trp Thr Arg Ile Thr Leu Trp Asn Arg Asp Leu Ala Pro Thr Pro Gly
        275                 280                 285
```

```
Ala Asn Leu Tyr Gly Ser His Pro Phe Tyr Leu Ala Leu Glu Asp Gly
290                 295                 300

Gly Ser Ala His Gly Val Phe Leu Leu Asn Ser Asn Ala Met Asp Val
305                 310                 315                 320

Val Leu Gln Pro Ser Pro Ala Leu Ser Trp Arg Ser Thr Gly Gly Ile
                325                 330                 335

Leu Asp Val Tyr Ile Phe Leu Gly Pro Glu Pro Lys Ser Val Val Gln
                340                 345                 350

Gln Tyr Leu Asp Val Val Gly Tyr Pro Phe Met Pro Pro Tyr Trp Gly
        355                 360                 365

Leu Gly Phe His Leu Cys Arg Trp Gly Tyr Ser Ser Thr Ala Ile Thr
370                 375                 380

Arg Gln Val Val Glu Asn Met Thr Arg Ala His Phe Pro Leu Asp Val
385                 390                 395                 400

Gln Trp Asn Asp Leu Asp Tyr Met Asp Ser Arg Arg Asp Phe Thr Phe
                405                 410                 415

Asn Lys Asp Gly Phe Arg Asp Phe Pro Ala Met Val Gln Glu Leu His
                420                 425                 430

Gln Gly Gly Arg Arg Tyr Met Met Ile Val Asp Pro Ala Ile Ser Ser
        435                 440                 445

Ser Gly Pro Ala Gly Ser Tyr Arg Pro Tyr Asp Glu Gly Leu Arg Arg
450                 455                 460

Gly Val Phe Ile Thr Asn Glu Thr Gly Gln Pro Leu Ile Gly Lys Val
465                 470                 475                 480

Trp Pro Gly Ser Thr Ala Phe Pro Asp Phe Thr Asn Pro Thr Ala Leu
                485                 490                 495

Ala Trp Trp Glu Asp Met Val Ala Glu Phe His Asp Gln Val Pro Phe
        500                 505                 510

Asp Gly Met Trp Ile Asp Met Asn Glu Pro Ser Asn Phe Ile Arg Gly
        515                 520                 525

Ser Glu Asp Gly Cys Pro Asn Asn Glu Leu Glu Asn Pro Pro Tyr Val
530                 535                 540

Pro Gly Val Val Gly Gly Thr Leu Gln Ala Ala Thr Ile Cys Ala Ser
545                 550                 555                 560

Ser His Gln Phe Leu Ser Thr His Tyr Asn Leu His Asn Leu Tyr Gly
                565                 570                 575

Leu Thr Glu Ala Ile Ala Ser His Arg Ala Leu Val Lys Ala Arg Gly
                580                 585                 590

Thr Arg Pro Phe Val Ile Ser Arg Ser Thr Phe Ala Gly His Gly Arg
        595                 600                 605

Tyr Ala Gly His Trp Thr Gly Asp Val Trp Ser Ser Trp Glu Gln Leu
610                 615                 620

Ala Ser Ser Val Pro Glu Ile Leu Gln Phe Asn Leu Leu Gly Val Pro
625                 630                 635                 640

Leu Val Gly Ala Asp Val Cys Gly Phe Leu Gly Asn Thr Ser Glu Glu
                645                 650                 655

Leu Cys Val Arg Trp Thr Gln Leu Gly Ala Phe Tyr Pro Phe Met Arg
        660                 665                 670

Asn His Asn Ser Leu Leu Ser Leu Pro Gln Glu Pro Tyr Ser Phe Ser
                675                 680                 685

Glu Pro Ala Gln Gln Ala Met Arg Lys Ala Leu Thr Leu Arg Tyr Ala
690                 695                 700

Leu Leu Pro His Leu Tyr Thr Leu Phe His Gln Ala His Val Ala Gly
```

-continued

```
              705                710                715                720
Glu Thr Val Ala Arg Pro Leu Phe Leu Glu Phe Pro Lys Asp Ser Ser
                    725                730                735
Thr Trp Thr Val Asp His Gln Leu Leu Trp Gly Ala Leu Leu Ile
                740                745                750
Thr Pro Val Leu Gln Ala Gly Lys Ala Glu Val Thr Gly Tyr Phe Pro
                755                760                765
Leu Gly Thr Trp Tyr Asp Leu Gln Thr Val Pro Val Glu Ala Leu Gly
            770                775                780
Ser Leu Pro Pro Pro Ala Ala Pro Arg Glu Pro Ala Ile His Ser
785                790                795                800
Glu Gly Gln Trp Val Thr Leu Pro Ala Pro Leu Asp Thr Ile Asn Val
                    805                810                815
His Leu Arg Ala Gly Tyr Ile Ile Pro Leu Gln Gly Pro Gly Leu Thr
                820                825                830
Thr Thr Glu Ser Arg Gln Gln Pro Met Ala Leu Ala Val Ala Leu Thr
                835                840                845
Lys Gly Gly Glu Ala Arg Gly Glu Leu Phe Trp Asp Asp Gly Glu Ser
            850                855                860
Leu Glu Val Leu Glu Arg Gly Ala Tyr Thr Gln Val Ile Phe Leu Ala
865                870                875                880
Arg Asn Asn Thr Ile Val Asn Glu Leu Val Arg Val Thr Ser Glu Gly
                    885                890                895
Ala Gly Leu Gln Leu Gln Lys Val Thr Val Leu Gly Val Ala Thr Ala
                900                905                910
Pro Gln Gln Val Leu Ser Asn Gly Val Pro Val Ser Asn Phe Thr Tyr
            915                920                925
Ser Pro Asp Thr Lys Val Leu Asp Ile Cys Val Ser Leu Leu Met Gly
            930                935                940
Glu Gln Phe Leu Val Ser Trp Cys
945                950
```

HIGHLY POTENT ACID ALPHA-GLUCOSIDASE WITH ENHANCED CARBOHYDRATES

CROSS-REFERENCE TO RELATED APPLICATIONS

This application is a continuation of U.S. patent application Ser. No. 17/249,175, filed Feb. 23, 2021, which is a division of U.S. patent application Ser. No. 16/252,505, filed Jan. 18, 2019 and issued as U.S. Pat. No. 10,961,522, which is a continuation of U.S. patent application Ser. No. 15/515,808, filed Mar. 30, 2017 and issued as U.S. Pat. No. 10,208,299, which is the U.S. national stage entry under 35 U.S.C. § 371 of International Application No. PCT/US2015/053252, filed Sep. 30, 2015, which claims the benefit of priority to U.S. Provisional Application No. 62/057,842, filed Sep. 30, 2014, U.S. Provisional Application No. 62/057,847, filed Sep. 30, 2014, U.S. Provisional Application No. 62/112,463, filed Feb. 5, 2015, and U.S. Provisional Application No. 62/135,345, filed Mar. 19, 2015, each of which is incorporated by reference in its entirety.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: AMCS_005_07US_SeqList_ST25.txt, date recorded: Feb. 4, 2022, file size ~40,505 bytes).

BACKGROUND OF THE INVENTION

Field of the Invention

The present invention involves the fields of medicine, genetics and recombinant glycoprotein biochemistry, and, specifically, relates to recombinant human alpha glucosidase (rhGAA) compositions that have a higher total content of mannose 6-phosphate-bearing glycans that efficiently target CIMPR on muscle cells and subsequently deliver rhGAA to the lysosomes where it can break down abnormally high levels of accumulated glycogen. The rhGAA of the invention exhibits superior targeting to muscle cells and subsequent delivery to lysosomes compared to conventional rhGAA products and exhibits other pharmacokinetic properties that make it particularly effective for enzyme replacement therapy of subjects having Pompe disease.

Description of the Related Art

Existing enzyme replacement therapies for Pompe Disease use conventional rhGAA products that have a low total content of M6P and bis-M6P bearing glycans. Conventional Alglucosidase Alfa products are sold under the trademarks LUMIZYME® and MYOZYME®. LUMIZYME® and MYOZYME® are conventional forms of rhGAA produced or marketed as biologics by Genzyme and approved by the U.S. Food and Drug Administration and are described by reference to the *Physician's Desk Reference* (2014) (which is hereby incorporated by reference) or by their prescription labels approved for use in the United States by the FDA as of Oct. 1, 2014. Alglucosidase Alfa is identified as chemical name [199-arginine,223-histidine]prepro-α-glucosidase (human); molecular formula, $C_{4758}H_{7262}N_{1274}O_{1369}S_{35}$; CAS number 420794-05-0. These products are administered to subjects with Pompe Disease, also known as glycogen storage disease type II (GSD-II) or acid maltase deficiency disease. Enzyme replacement therapy seeks to treat Pompe Disease by replacing the missing GAA in lysosomes by administering rhGAA thus restoring the ability of cell to break down lysosomal glycogen.

Pompe disease is an inherited lysosomal storage disease that results from a deficiency in acid α-glucosidase (GAA) activity. A person having Pompe Disease lacks or has reduced levels of acid alpha-glucosidase (GAA), the enzyme which breaks down glycogen, and a substance the body uses as an energy source. This enzyme deficiency causes excess glycogen accumulation in the lysosomes, which are intracellular organelles containing enzymes that ordinarily break down glycogen and other cellular debris or waste products. Glycogen accumulation in certain tissues of a subject having Pompe Disease, especially muscles, impairs the ability of cells to function normally. In Pompe Disease, glycogen is not properly metabolized and progressively accumulates in the lysosomes, especially in skeletal muscle cells and, in the infant onset form of the disease, in cardiac muscle cells. The accumulation of glycogen damages the muscle and nerve cells as well as those in other affected tissues.

Traditionally, depending on the age of onset, Pompe disease is clinically recognized as either an early infantile form or as a late onset form. The age of onset tends to parallel the severity of the genetic mutation causing Pompe Disease. The most severe genetic mutations cause complete loss of GAA activity manifest as early onset disease during infancy. Genetic mutations that diminish GAA activity but do not completely eliminate it are associated with forms of Pompe disease having delayed onset and progression. Infantile onset Pompe disease manifests shortly after birth and is characterized by muscular weakness, respiratory insufficiency and cardiac failure. Untreated, it is usually fatal within two years. Juvenile and adult onset Pompe disease manifest later in life and usually progress more slowly than infantile onset disease. This form of the disease, while it generally does not affect the heart, may also result in death, due to weakening of skeletal muscles and those involved in respiration.

Current non-palliative treatment of Pompe disease involves enzyme replacement therapy (ERT) using recombinant human GAA (rhGAA) such as LUMIZYME® or MYOZYME®. The rhGAA is administered in an attempt to replace or supplement the missing or defective GAA in a subject having Pompe Disease. However, since most of the rhGAA in conventional rhGAA products does not target muscle tissue it is non-productively eliminated after administration.

This occurs because conventional rhGAAs lack a high total content of M6P- and bis-M6P-bearing glycans which target a rhGAA molecule to the CIMPR on target muscle cells where it is subsequently transported into the cell's lysosomes. This cellular uptake of rhGAA for enzyme replacement therapy is facilitated by the specialized carbohydrate, mannose-6-phosphate (M6P), which binds to the cation-independent mannose 6-phosphate receptor (CIMPR) present on cell surfaces for subsequent delivery of the exogenous enzyme to lysosomes.

There are seven potential N-linked glycosylation sites on rhGAA. Since each glycosylation site is heterogeneous in the type of N-linked oligosaccharides (N-glycans) present, rhGAA consist of a complex mixture of proteins with N-glycans having varying binding affinities for M6P receptor and other carbohydrate receptors. rhGAA that contains a high mannose N-glycans having one M6P group (mono- M6P) binds to CIMPR with low (~6,000 nM) affinity while rhGAA that contains two M6P groups on same N-glycan (bis-M6P) bind with high (~2 nM) affinity. Representative structures for non-phosphorylated, mono-M6P, and bis-M6P glycans are shown by FIG. 1A. The mannose-6-P group is shown by FIG. 1B. Once inside the lysosome, rhGAA can enzymatically degrade accumulated glycogen. However, conventional rhGAAs have low total levels of M6P- and bis-M6P-bearing glycans and, thus, target muscle cells poorly resulting in inferior delivery of rhGAA to the lysosomes. The majority of rhGAA molecules in these conventional products do not have phosphorylated N-glycans, thereby lacking affinity for the CIMPR. Non-phosphorylated high mannose glycans can also be cleared by the mannose receptor which results in non-productive clearance of the ERT (FIG. 2).

The other type of N-glycans, complex carbohydrates, which contain, galactose and sialic acids are also present on rhGAA. Since complex N-glycans are not phosphorylated they have no affinity for CIMPR. However, complex-type N-glycans with exposed galactose residues have moderate to high affinity for the asialoglycoprotein receptor on liver hepatocytes which leads to rapid non-productive clearance of rhGAA (FIG. 2).

The glycosylation of GAA or rhGAA can be enzymatically modified in vitro by the phosphotransferase and uncovering enzymes described by Canfield, et al., U.S. Pat. No. 6,534,300, to generate M6P groups. Enzymatic glycosylation cannot be adequately controlled and produces rhGAA having undesirable immunological and pharmacological properties. Enzymatically modified rhGAA may contain only high-mannose N-glycans which all could be potentially enzymatically phosphorylated in vitro with a phosphotransferase/uncovering enzyme and may contain on average 5-6 M6P groups per GAA. The glycosylation patterns produced by in vitro enzymatic treatment of GAA are problematic because the additional terminal mannose residues, particularly non-phosphorylated terminal mannose residues, negatively affect the pharmacokinetics of the modified rhGAA. When such an enzymatically modified product is administered in vivo, these mannose groups increase non-productive clearance of the GAA, increase the uptake of the enzymatically-modified GAA by immune cells, and reduce rhGAA therapeutic efficacy due to less of the GAA reaching targeted tissues, such as cardiac or skeletal muscle myocytes. For example, terminal non-phosphorylated mannose residues are known ligands for mannose receptors in the liver and spleen which leads to rapid clearance of the enzymatically-modified rhGAA and reduced targeting of rhGAA to target tissue. Moreover, the glycosylation pattern of enzymatically-modified GAA having high mannose N-glycans with terminal non-phosphorylated mannose residues resembles that on glycoproteins produced in yeasts, molds and function increasing the risk of triggering immune or allergic responses, such as life-threatening severe allergic (anaphylactic) or hypersensitivity reactions, to the enzymatically modified rhGAA.

As explained above, conventional rhGAA products like LUMIZYME® have low levels of mono-phosphorylated glycans and even lower bis-phosphorylated glycans. In order for a Pompe disease therapy to be efficacious rhGAA must be delivered to the lysosomes in muscle cells. The low total amount of mono-M6P and bis-M6P targeting groups on conventional rhGAA limits cellular uptake via CIMPR and lysosomal delivery, thus making conventional enzyme replacement therapy inefficient. For example, while conventional rhGAA products at 20 mg/kg or higher doses do ameliorate some aspects of Pompe disease, they are not able to adequately reduce accumulated glycogen in many target tissues, particularly skeletal muscles to reverse disease progression.

Due to the inefficiency of delivering conventional enzyme replacement therapies to lysosomes, such therapies are often associated with other problems, including generation of immune responses to GAA. A large portion of the GAA in a conventional rhGAA does not contain glycans bearing mono- or bis-M6P, which target the rhGAA to muscle cells. A subject's immune system is exposed to this excess non-phosphorylated GAA and can generate detrimental immune responses that recognize GAA. Induction of an immune responses to the non-phosphorylated GAA that does not enter the target tissues and deliver to the lysosomes increase the risk of treatment failure due to immunological inactivation of the administered rhGAA and increases the risk of the patient experiencing detrimental autoimmune or allergic reactions to the rhGAA treatment. The rhGAA according to the invention contains significantly less of this non-targeted, non-phosphorylated rhGAA, thus reducing exposure of a patient's immune system to it.

Logistically, larger doses impose additional burdens on the subject as well as medical professionals treating the subject, such as lengthening the infusion time needed to administer rhGAA intravenously. This is because conventional rhGAA's contain a higher content of non-phosphorylated rhGAA which does not target the CIMPR on muscle cells. rhGAA that does not bind to CIMPR on muscle cells and then enter the lysosome does not enzymatically degrade glycogen there. When equivalent doses of a conventional rhGAA and the rhGAA according to the invention are administered, more rhGAA in the composition according to the invention binds CIMPR on muscle cells and then delivers to the lysosome. The rhGAA of the invention provides a doctor with the option of administering a lower amount of rhGAA while delivering the same or more rhGAA to the lysosome.

Current manufacturing processes used to make conventional rhGAA, such as MYOZYME® or LUMIZYME®, have not significantly increased the content of M6P or bis-M6P because cellular carbohydrate processing is naturally complex and extremely difficult to manipulate. In view of these deficiencies of conventional rhGAA products, the inventors diligently sought and identified ways to efficiently target rhGAA to muscle cells and deliver it to the lysosome, minimize non-productive clearance of rhGAA once administered, and thus more productively target rhGAA to muscle tissue.

BRIEF SUMMARY OF THE INVENTION

In response to the problems associated with targeting and administering conventional forms of rhGAA and to the difficulties associated with producing such well-targeted forms of rhGAA, the inventors have investigated and developed procedures for making rhGAA that more efficiently targets the CIMPR and deliver it to lysosomes in muscle tissues because it has a higher content of M6P- and bis-M6P glycan than conventional rhGAA compositions. Moreover, rhGAA of the invention has well-processed complex-type N-glycans which minimize non-productive clearance of the rhGAA by non-target tissues.

Taking into account the problems associated with current enzyme replacement treatments using conventional rhGAA products such as LUMIZYME®, through diligent study and investigation the inventors have developed a method for producing rhGAA in CHO cells having significantly higher total content of mono-M6P and bis-M6P glycans which target CIMPR on muscle cells and then deliver the rhGAA to the lysosomes.

The rhGAA produced by this method also has advantageous pharmacokinetic properties by virtue of its overall glycosylation pattern that increases target tissue uptake and decreases non-productive clearance following administration to a subject having Pompe Disease. The inventors show that the rhGAA of the invention, as exemplified by rhGAA designated as ATB-200, is more potent in and more efficient at targeting skeletal muscle tissues than conventional rhGAA such as LUMIZYME®. The rhGAA according to the invention has a superior ability to productively target muscle tissues in patients having Pompe Disease and reduce non-productive clearance of rhGAA as illustrated by FIG. 2.

The superior rhGAA according to the invention may be further completed or combined with chaperones or conjugated to other groups that target the CIMPR in muscle tissue, such as portions of IGF2 that bind to this receptor. The Examples below show that the rhGAA of the invention, exemplified by ATB-200 rhGAA, exceeds the existing standard of care for enzyme replacement therapy by providing significantly better glycogen clearance in skeletal muscle as compared to existing regimen using the conventional rhGAA product LUMIZYME®.

BRIEF DESCRIPTION OF THE DRAWINGS

FIG. 3A graphically depicts a CIMPR receptor (also known as an IGF2 receptor) and domains of this receptor. FIG. 3B is a table showing binding affinity (nMolar) of glycans bearing bis- and mono-M6P for CIMPR, the binding affinity of high mannose-type glycans to mannose receptors, and the binding affinity of de-sialyated complex glycan for asialyoglycoprotein receptors. RhGAA that has glycans bearing M6P and bis-M6P can productively bind to CIMPR on muscle target cells. RhGAA that has high mannose glycans and de-sialylated glycans can non-productively bind to non-target cells bearing the corresponding receptors.

As shown in FIG. 4A, 78% of the GAA activity in LUMIZYME® eluted prior to addition of M6P. FIG. 4B shows that 73% of the GAA MYOZYME® activity eluted prior to addition of M6P. Only 22% or 27% of the rhGAA in LUMIZYME® or MYOZYME®, respectively, was eluted with M6P. These figures show that most of the rhGAA in these two conventional rhGAA products lack glycans having M6P needed to target CIMPR in target muscle tissues.

FIG. 9 shows a summary of N-glycan structures of LUMIZYME® compared to three different preparations of ATB200 rhGAA, identified as BP-rhGAA, ATB200-1 and ATB200-2.

FIG. 11A compares ATB-200 rhGAA activity (left trace; diamonds) with LUMIZYME® rhGAA activity (right trace; circles) inside normal fibroblasts at various GAA concentrations, and shows ATB-200 rhGAA activity (triangle) compared to LUMIZYME® activity (square) in the presence of M6P. FIG. 11B compares ATB-200 rhGAA activity (left trace; diamonds) with LUMIZYME® rhGAA activity (right trace; circles) inside fibroblasts from a subject having Pompe Disease at various GAA concentrations, and shows ATB-200 rhGAA activity (triangle) compared to LUMIZYME® activity (square) in the presence of M6P. FIG. 11C compares ($K_{uptake}$) of fibroblasts from normal subjects and subjects with Pompe Disease.

FIG. 16C: Evaluation of lysosomal proliferation by LAMP-1 marker. FIG. 16D: Identification of Type I and Type II muscle fibers.

FIGS. 17A-17B show improvement of Skeletal Muscle Pathology in Mice treated with ATB-200+Miglustat (AT2221) over those treated with ERT alone. PAS glycogen staining (FIG. 17A) of muscle tissue from GAA KO mice treated with conventional rhGAA or ATB-200 rhGAA and miglustat (AT-2221). FIG. 17B: Evaluation of lysosomal proliferation by LAMP-1 marker.

DETAILED DESCRIPTION OF THE INVENTION

Figure 1A:
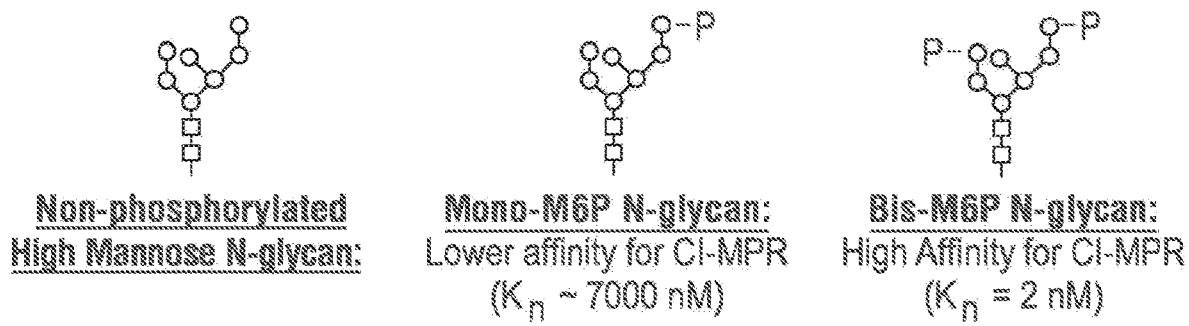
FIG. 1A shows a non-phosphorylated high mannose glycan, a mono-M6P glycan, and a bis-M6P glycan.
Figure 1B:
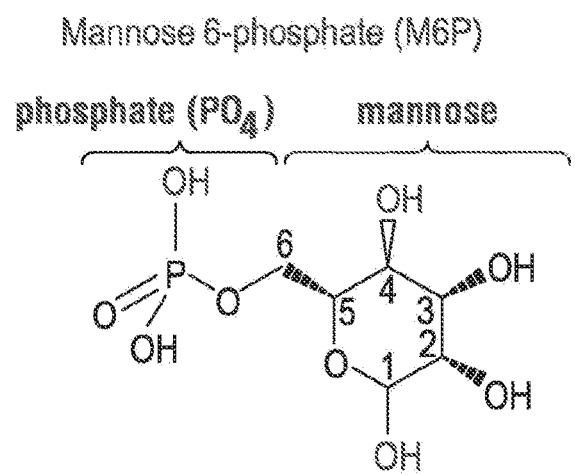
FIG. 1B shows the chemical structure of the M6P group.

Definitions: The terms used in this specification generally have their ordinary meanings in the art, within the context of this invention and in the specific context where each term is used. Certain terms are discussed below, or elsewhere in the specification, to provide additional guidance to the practitioner in describing the compositions and methods of the invention and how to make and use them.

The term "GAA" refers to human acid α-glucosidase (GAA) an enzyme that catalyzes the hydrolysis of α-1,4- and α-1,6-glycosidic linkages of lysosomal glycogen as well as to insertional, relational or substitution variants of the GAA amino acid sequence and fragments of a longer GAA sequence that exert enzymatic activity. The term "rhGAA" is used to distinguish endogenous GAA from synthetic or recombinant-produced GAA, such as that produced by transformation of CHO cells with DNA encoding GAA. An exemplary DNA sequence encoding GAA is SEQ ID NO: 2, which is incorporated by reference. GAA and rhGAA may be present in a composition containing a mixture of GAA molecules having different glycosylation patterns, such as a mixture of rhGAA molecules bearing mono-M6P or bis-M6P groups on their glycans and GAA molecules that do not bear M6P or bis-M6P. GAA and rhGAA may also be completed with other compounds, such as chaperones, or may be bound to other moieties in a GAA or rhGAA conjugate, such as bound to an IGF2 moiety that targets the conjugate to CIMPR and subsequently delivers it to the lysosomes.

A "subject" or "patient" is preferably a human, though other mammals and non-human animals having disorders involving accumulation of glycogen may also be treated. A subject may be a fetus, a neonate, child, juvenile or an adult with Pompe disease or other glycogen storage or accumulation disorder. One example of an individual being treated is an individual (fetus, neonate, child, juvenile, adolescent, or adult human) having GSD-II (e.g., infantile GSD-II, juvenile GSD-II, or adult-onset GSD-II). The individual can have residual GAA activity, or no measurable activity. For example, the individual having GSD-II can have GAA activity that is less than about 1% of normal GAA activity (infantile GSD-II), GAA activity that is about 1-10% of normal GAA activity (juvenile GSD-II), or GAA activity that is about 10-40% of normal GAA activity (adult GSD-II).

The terms, "treat" and "treatment," as used herein, refer to amelioration of one or more symptoms associated with the disease, prevention or delay of the onset of one or more symptoms of the disease, and/or lessening of the severity or frequency of one or more symptoms of the disease. For example, treatment can refer to improvement of cardiac status (e.g., increase of end-diastolic and/or end-systolic volumes, or reduction, amelioration or prevention of the progressive cardiomyopathy that is typically found in GSD-II) or of pulmonary function (e.g., increase in crying vital capacity over baseline capacity, and/or normalization of oxygen desaturation during crying); improvement in neurodevelopment and/or motor skills (e.g., increase in AIMS score); reduction of glycogen levels in tissue of the individual affected by the disease; or any combination of these effects. In one preferred embodiment, treatment includes improvement of cardiac status, particularly in reduction or prevention of GSD-II-associated cardiomyopathy.

The terms, "improve," "increase" or "reduce," as used herein, indicate values that are relative to a baseline measurement, such as a measurement in the same individual prior to initiation of the treatment described herein, or a measurement in a control individual (or multiple control individuals) in the absence of the treatment described herein. A control individual is an individual afflicted with the same form of GSD-II (either infantile, juvenile or adult-onset) as the individual being treated, who is about the same age as the individual being treated (to ensure that the stages of the disease in the treated individual and the control individual(s) are comparable).

The term "purified" as used herein refers to material that has been isolated under conditions that reduce or eliminate the presence of unrelated materials, i.e., contaminants, including native materials from which the material is obtained. For example, a purified protein is preferably substantially free of other proteins or nucleic acids with which it is associated in a cell; a purified nucleic acid molecule is preferably substantially free of proteins or other unrelated nucleic acid molecules with which it can be found within a cell. As used herein, the term "substantially free" is used operationally, in the context of analytical testing of the material. Preferably, purified material substantially free of contaminants is at least 95% pure; more preferably, at least 97% pure, and more preferably still at least 99% pure. Purity can be evaluated by chromatography, gel electrophoresis, immunoassay, composition analysis, biological assay, enzymatic assay and other methods known in the art. In a specific embodiment, purified means that the level of contaminants is below a level acceptable to regulatory authorities for safe administration to a human or non-human animal. Recombinant proteins may be isolated or purified from CHO cells using methods known in the art including by chromatographic size separation, affinity chromatography or anionic exchange chromatography.

The term "genetically modified" or "recombinant" refers to cells, such as CHO cells, that express a particular gene product, such as rhGAA or ATB-200 rhGAA, following introduction of a nucleic acid comprising a coding sequence which encodes the gene product, along with regulatory elements that control expression of the coding sequence. Introduction of the nucleic acid may be accomplished by any method known in the art including gene targeting and homologous recombination. As used herein, the term also includes cells that have been engineered to express or overexpress an endogenous gene or gene product not normally expressed by such cell, e.g., by gene activation technology.

"Pompe Disease" refers to an autosomal recessive LSD characterized by deficient acid alpha glucosidase (GAA) activity which impairs lysosomal glycogen metabolism. The enzyme deficiency leads to lysosomal glycogen accumulation and results in progressive skeletal muscle weakness, reduced cardiac function, respiratory insufficiency, and/or CNS impairment at late stages of disease. Genetic mutations in the GAA gene result in either lower expression or produce mutant forms of the enzyme with altered stability, and/or biological activity ultimately leading to disease. (see generally Hirschhorn R, 1995, Glycogen Storage Disease Type II: Acid α-Glucosidase (Acid Maltase) Deficiency, The Metabolic and Molecular Bases of Inherited Disease, Scriver et al., eds., McGraw-Hill, New York, 7th ed., pages 2443-2464). The three recognized clinical forms of Pompe Disease (infantile, juvenile and adult) are correlated with the level of residual α-glucosidase activity (Reuser A J et al., 1995, Glycogenosis Type II (Acid Maltase Deficiency), Muscle & Nerve Supplement 3, S61-S69). Infantile Pompe disease (type I or A) is most common and most severe, characterized by failure to thrive, generalized hypotonic, cardiac hypertrophy, and cardiorespiratory failure within the second year of life. Juvenile Pompe disease (type II or B) is intermediate in severity and is characterized by a predominance of muscular symptoms without cardiomegaly. Juvenile Pompe individuals usually die before reaching 20 years of age due to respiratory failure. Adult Pompe disease (type III or C) often presents as a slowly progressive myopathy in the teenage years or as late as the sixth decade (Felicia K J et al., 1995, Clinical Variability in Adult-Onset Acid Maltase Deficiency: Report of Affected Sibs and Review of the Literature, Medicine 74, 131-135). In Pompe, it has been shown that α-glucosidase is extensively modified post-translationally by glycosylation, phosphorylation, and proteolytic processing. Conversion of the 110 kilo Dalton (kids) precursor to 76 and 70 kids mature forms by proteolysis in the lysosome is required for optimum glycogen catalysis. As used herein, the term "Pompe Disease" refers to all types of Pompe Disease. The formulations and dosing regimens disclosed in this application may be used to treat, for example, Type I, Type II or Type III Pompe Disease.

Non-Limiting Embodiments of the Invention

A rhGAA composition derived from CHO cells that contains a higher amount of rhGAA containing N-glycans carrying mono-mannose-6-phosphate (M6P) or bis-M6P than conventional rhGAA as exemplified by LUMIZYME®. An exemplary rhGAA composition according to the invention is ATB-200 (sometimes designated ATB-200, ATB-200 or CBP-rhGAA) which is described in the Examples. The rhGAA of the invention (ATB-200) has been shown to bind the CIMPR with high affinity ($K_D$~2-4 nM) and to be efficiently internalized by Pompe fibroblasts and skeletal muscle myoblasts ($K_{uptake}$~7-14 nM). ATB-200 was characterized in vivo and shown to have a shorter apparent plasma half-life ($t_{1/2}$~45 min) than the current rhGAA ERT ($t_{1/2}$~60 min).

The amino acid sequence of the rhGAA can be at least 70%, 75%, 80%, 85%, 95% or 99% identical, or contain 1, 2, 3, 4, 5, 6, 7, 8, 9, 10 or more deletions, substitutions or additions to the amino acid sequence described by SEQ ID NO: 1, 3 or 4. In some embodiments of the GAA or rhGAA of the invention, such as in ATB-200 rhGAA, the GAA or rhGAA will comprise a wild-type GAA amino acid sequence such as that of SEQ ID NO: 1 or 3. In other non-limiting embodiments, the rhGAA comprises a subset of the amino acid residues present in a wild-type GAA, wherein the subset includes the amino acid residues of the wild-type GAA that form the active site for substrate binding and/or substrate reduction. In one embodiment, the rhGAA is glucosidase alfa, which is the human enzyme acid α-glucosidase (GAA), encoded by the most predominant of nine observed haplotypes of this gene. The rhGAA of the invention, including ATB-200 rhGAA, may comprise an amino acid sequence that is 90%, 95%, 96%, 97%, 98%, or 99% identical to the amino acid sequence of human alpha glucosidase, such as that given by accession number AHE24104.1 (GI:568760974)(SEQ ID NO: 1) and which is incorporated by reference to U.S. Pat. No. 8,592,362 or to the amino acid sequence of NP_000143.2 (SEQ ID NO: 4). A nucleotide and amino acid sequence for GAA is also given by SEQ ID NOS: 2 and 3, respectively. Variants of this amino acid sequence also include those with 1, 2, 3, 4, 5, 6, 7, 8, 9, 10, 11, 12 or more amino acid deletions, insertions or substitutions to the GAA amino acid sequence below. Polynucleotide sequences encoding GAA and such variant human GAAs are also contemplated and may be used to recombinantly express rhGAAs according to the invention.

Various alignment algorithms and/or programs may be used to calculate the identity between two sequences, including FASTA, or BLAST which are available as a part of the GCG sequence analysis package (University of Wisconsin, Madison, Wis.), and can be used with, e.g., default setting. For example, polypeptides having at least 70%, 85%, 90%, 95%, 98% or 99% identity to specific polypeptides described herein and preferably exhibiting substantially the same functions, as well as polynucleotide encoding such polypeptides, are contemplated. Unless otherwise indicated a similarity score will be based on use of BLOSUM62. When BLASTP is used, the percent similarity is based on the BLASTP positives score and the percent sequence identity is based on the BLASTP identities score. BLASTP "Identities" shows the number and fraction of total residues in the high scoring sequence pairs which are identical; and BLASTP "Positives" shows the number and fraction of residues for which the alignment scores have positive values and which are similar to each other. Amino acid sequences having these degrees of identity or similarity or any intermediate degree of identity of similarity to the amino acid sequences disclosed herein are contemplated and encompassed by this disclosure. The polynucleotide sequences of similar polypeptides are deduced using the genetic code and may be obtained by conventional means, in particular by reverse translating its amino acid sequence using the genetic code.

Preferably, no more than 70, 65, 60, 55, 45, 40, 35, 30, 25, 20, 15, 10, or 5% of the total rhGAA in the composition according to the invention lacks an N-glycan bearing M6P or bis-M6P or lacks a capacity to bind to the cationic independent mannose-6-phosphate receptor (CIMPR). Alternatively, 30, 35, 40, 45, 50, 55, 60, 65, 70, 75, 80, 85, 90, 95, 99%, <100% or more of the rhGAA in the composition comprises at least one N-glycan bearing M6P and/or bis-M6P or has the capacity to bind to CIMPR.

The rhGAA molecules in the rhGAA composition of the invention may have 1, 2, 3 or 4 M6P groups on their glycans. For example, only one N-glycan on an rhGAA molecule may bear M6P (mono-phosphorylated), a single N-glycan may bear two M6P groups (bis-phosphorylated), or two different N-glycans on the same rhGAA molecule may bear single M6P groups. rhGAA molecules in the rhGAA composition may also have N-glycans bearing no M6P groups. In another embodiment, on average the N-glycans contain greater than 3 mol/mol of M6P and greater than 4 mol/mol sialic acid. On average at least about 3, 4, 5, 6, 7, 8, 9, or 10% of the total glycans on the rhGAA may be in the form of a mono-M6P glycan, for example, about 6.25% of the total glycans may carry a single M6P group and on average, at least about 0.5, 1, 1.5, 2.0, 2.5, 3.0% of the total glycans on the rhGAA are in the form of a bis-M6P glycan and on average less than 25% of total rhGAA of the invention contains no phosphorylated glycan binding to CIMPR.

The rhGAA composition according to the invention may have an average content of N-glycans carrying M6P ranging from 0.5 to 7.0 mol/mol rhGAA or any intermediate value of subrange including 0.5, 1.0, 1.5, 2.0, 2.5, 3.0, 3.5, 4.0, 4.5, 5.0, 5.5, 6.0, 6.5, or 7.0 mol/mol rhGAA. As shown in the Examples, the rhGAA of the invention can be fractionated to provide rhGAA compositions with different average numbers of M6P-bearing or bis-M6P-bearing glycans on the rhGAA thus permitting further customization of rhGAA targeting to the lysosomes in target tissues by selecting a particular fraction or by selectively combining different fractions.

Up to 60% of the N-glycans on the rhGAA may be fully sialyated, for example, up to 10%, 20%, 30%, 40%, 50% or 60% of the N-glycans may be fully sialyated. In some embodiments from 4 to 20% of the total N-glycans in the rhGAA composition are fully sialylated.

In other embodiments no more than 5%, 10%, 20% or 30% of N-glycans on the rhGAA carry sialic acid and a terminal Gal. This ranges includes all intermediate values and subranges, for example, 7 to 30% of the total N-glycans on the rhGAA in the composition can carry sialic acid and terminal Gal.

In yet other embodiments, no more than 5, 10, 15, 16, 17, 18, 19 or 20% of the N-glycans on the rhGAA have a terminal Gal only and do not contain sialic acid. This range includes all intermediate values and subranges, for example, from 8 to 19% of the total N-glycans on the rhGAA in the composition may have terminal Gal only and do not contain sialic acid.

In other embodiments of the invention 40, 45, 50, 55 to 60% of the total N-glycans on the rhGAA in the composition are complex type N-glycans; or no more than 1, 2, 3, 4, 5, 6, 7% of total N-glycans on the rhGAA in the composition are hybrid-type N-glycans; no more than 5, 10, or 15% of the high mannose-type N-glycans on the rhGAA in the composition are non-phosphorylated; at least 5% or 10% of the high mannose-type N-glycans on the rhGAA in the composition are mono-M6P phosphorylated; and/or at least 1 or 2% of the high mannose-type N-glycans on the rhGAA in the composition are bis-M6P phosphorylated. These values include all intermediate values and subranges. An rhGAA composition according to the invention may meet one or more of the content ranges described above.

In some embodiments, the rhGAA composition of the invention will bear, on average, 2.0 to 8.0 sialic acid residues per mol of rhGAA. This range includes all intermediate values and subranges including 2.0, 2.5, 3.0, 3.5, 4.0, 4.5, 5.0, 5.5, 6.0, 6.5, 7.0, 7.5 and 8.0 residues/mol rhGAA. Sialic acid residues may prevent non-productive clearance by asialoglycoprotein receptors.

The rhGAA composition of the invention is preferably produced by CHO cells, such as CHO cell line GA-ATB-200, or by a subculture or derivative of such a CHO cell culture. DNA constructs, which express allelic variants of GAA or other variant GAA amino acid sequences such as those that are at least 90%, 95% or 99% identical to SEQ ID NO: 1, may be constructed and expressed in CHO cells. Those of skill in the art can select alternative vectors suitable for transforming CHO cells for production of such DNA constructs.

The inventors have found that rhGAA having superior ability to target the CIMPR and cellular lysosomes as well as glycosylation patterns that reduce its non-productive clearance in vivo can be produced using Chinese hamster ovary (CHO) cells. These cells can be induced to express rhGAA with significantly higher levels of total M6P and bis-M6P than conventional rhGAA products. The recombinant human GAA produced by these cells, for example, as exemplified by rhGAA ATB-200 described in the Examples, has significantly more muscle cell-targeting M6P and bis-M6P groups than conventional GAA, such as LUMIZYME® and has been shown to efficiently bind to CIMPR and be efficiently taken up by skeletal muscle and cardiac muscle. It has also been shown to have a glycosylation pattern that provides a favorable pharmacokinetic profile and reduces non-productive clearance in vivo.

The rhGAA according to the invention may be formulated as a pharmaceutical composition or used in the manufacture of a medicament for treatment of Pompe Disease or other conditions associated with a deficient of GAA. The compositions can be formulated with a physiologically acceptable carrier or excipient. The carrier and composition can be sterile and otherwise suit the mode of administration.

Suitable pharmaceutically acceptable carriers include but are not limited to water, salt solutions (e.g., NaCl), saline, buffered saline, alcohols, glycerol, ethanol, gum arabic, vegetable oils, benzyl alcohols, polyethylene glycols, gelatin, carbohydrates such as lactose, amylose or starch, sugars such as mannitol, sucrose, or others, dextrose, magnesium stearate, talc, silicic acid, fatty acid esters, hydroxymethylcellulose, polyvinyl pyrolidone, etc., as well as combinations thereof. The pharmaceutical preparations can, if desired, be mixed with auxiliary agents, e.g., surfactants, such as polysorbates like polysorbate 80, lubricants, preservatives, stabilizers, wetting agents, emulsifiers, salts for influencing osmotic pressure, buffers, coloring, flavoring and/or aromatic substances and the like which do not deleteriously react with the active compounds. In a preferred embodiment, a water-soluble carrier suitable for intravenous administration is used.

The composition or medicament, if desired, can also contain minor amounts of wetting or emulsifying agents, or pH buffering agents. The composition can be a liquid solution, suspension, emulsion, tablet, pill, capsule, sustained release formulation, or powder. The composition can also be formulated as a suppository, with traditional binders and carriers such as triglycerides. Oral formulation can include standard carriers such as pharmaceutical grades of mannitol, lactose, starch, magnesium stearate, polyvinyl pyrollidone, sodium saccharine, cellulose, magnesium carbonate, etc. In a preferred embodiment the rhGAA is administered by IV infusion.

The composition or medicament can be formulated in accordance with the routine procedures as a pharmaceutical composition adapted for administration to human beings. For example, in a preferred embodiment, a composition for intravenous administration is a solution in sterile isotonic aqueous buffer. Where necessary, the composition may also include a solubilizing agent and a local anesthetic to ease pain at the site of the injection. Generally, the ingredients are supplied either separately or mixed together in unit dosage faun, for example, as a dry lyophilized powder or water free concentrate in a hermetically sealed container such as an ampule or sachet indicating the quantity of active agent. Where the composition is to be administered by infusion, it can be dispensed with an infusion bottle containing sterile pharmaceutical grade water, saline or dextrose/water. Where the composition is administered by injection, an ampule of sterile water for injection or saline can be provided so that the ingredients may be mixed prior to administration.

The rhGAA can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

rhGAA (or a composition or medicament containing GAA) is administered by an appropriate route. In one embodiment, the GAA is administered intravenously. In other embodiments, GAA is administered by direct administration to a target tissue, such as to heart or skeletal muscle (e.g., intramuscular), or nervous system (e.g., direct injection into the brain; intraventricularly; intrathecally). More than one route can be used concurrently, if desired.

The rhGAA (or a composition or medicament containing GAA) is administered in a therapeutically effective amount (e.g., a dosage amount that, when administered at regular intervals, is sufficient to treat the disease, such as by ameliorating symptoms associated with the disease, preventing or delaying the onset of the disease, and/or also lessening the severity or frequency of symptoms of the disease, as described above). The amount which will be therapeutically effective in the treatment of the disease will depend on the nature and extent of the disease's effects, and can be determined by standard clinical techniques. In addition, in vitro or in vivo assays may optionally be employed to help identify optimal dosage ranges. The precise dose to be employed will also depend on the route of administration, and the seriousness of the disease, and should be decided according to the judgment of a practitioner and each patient's circumstances. Effective doses may be extrapolated from dose-response curves derived from in vitro or animal model test systems. In a preferred embodiment, the therapeutically effective amount is equal of less than 20 mg enzyme/kg body weight of the individual, preferably in the range of about 1-10 mg enzyme/kg body weight, and even more preferably about 10 mg enzyme/kg body weight or about 5 mg enzyme/kg body weight. The effective dose for a particular individual can be varied (e.g., increased or decreased) over time, depending on the needs of the individual. For example, in times of physical illness or stress, or if anti-GAA antibodies become present or increase, or if disease symptoms worsen, the amount can be increased.

The therapeutically effective amount of GAA (or composition or medicament containing GAA) is administered at regular intervals, depending on the nature and extent of the disease's effects, and on an ongoing basis. Administration at a "regular interval," as used herein, indicates that the therapeutically effective amount is administered periodically (as distinguished from a one-time dose). The interval can be determined by standard clinical techniques. In preferred embodiments, GAA is administered monthly, bimonthly; weekly; twice weekly; or daily. The administration interval for a single individual need not be a fixed interval, but can be varied over time, depending on the needs of the individual. For example, in times of physical illness or stress, if anti-GAA antibodies become present or increase, or if disease symptoms worsen, the interval between doses can be decreased. In some embodiments, a therapeutically effective amount of 5, 10, 20, 50, 100, or 200 mg enzyme/kg body weight is administered twice a week, weekly or every other week with or without a chaperone.

The GAA or rhGAA of the invention may be prepared for later use, such as in a unit dose vial or syringe, or in a bottle or bag for intravenous administration. Kits containing the GAA or rhGAA, as well as optional excipients or other active ingredients, such as chaperones or other drugs, may be enclosed in packaging material and accompanied by instructions for reconstitution, dilution or dosing for treating a subject in need of treatment, such as a patient having Pompe disease.

GAA (or a composition or medicament containing GAA) can be administered alone, or in conjunction with other agents, such as a chaperone. rhGAA with different degrees of glycosylation with mono-M6P or bis-M6P may be administered or combinations of rhGAAs with different degrees of M6P or bisM6P glycosylate administered.

In some embodiments the rhGAA composition of the invention will be complexed or admixed with a chaperone, such as AT-2220 or AT-2221. Chaperones, sometimes referred to as "pharmacological chaperones," are compounds that when complexed or coadministered with rhGAA modify its pharmacokinetics and other pharmacological properties. Representative chaperones exemplified herein include AT2221 (miglustat, N-butyl-deoxynojirimycin) and AT2220 (duvoglustat HCl, 1-deoxynojirimycin). Such complexing or admixing may occur outside the body or inside the body, for example, where separate dosages of the rhGAA and chaperone are administered. For example, targeting of active rhGAA, its fractions, or derivatives of the invention to CIMPR and subsequently to cellular lysosomes may be improved by combining it duvoglustat-HCl (AT2220, deoxynojirimycine, AT2220) or miglustat (AT2221, N-butyl-deoxynojirimycin). The Examples below show significant glycogen substrate reductions in key skeletal muscles of GAA-knock-out mice receiving the well-targeted rhGAA of the invention in combination with a chaperone.

Another aspect of the invention pertains to CHO cells or their derivatives or other equivalents that produce the rhGAA according to the invention. One example of such a CHO cell line is GA-ATB-200 or a subculture thereof that produces a rhGAA composition as described herein. Such CHO cell lines may contain multiple copies of a gene, such as 5, 10, 15, or 20 or more copies, of a polynucleotide encoding GAA.

The high M6P and bis-M6P rhGAA of the invention, such as ATB-200 rhGAA, can be produced by transforming CHO cells (Chinese hamster ovary cells) with a DNA construct that encodes GAA. While CHO cells have been previously used to make rhGAA, it was not appreciated that transformed CHO cells could be cultured and selected in a way that would produce rhGAA having a high content of M6P and bis-M6P glycans which target the CIMPR.

Surprisingly, the inventors found that it was possible to transform CHO cell lines, select transformants that produce rhGAA containing a high content of glycans bearing M6P or bis-M6P that target the CIMPR, and to stably express this high-M6P rhGAA. Thus, a related aspect of the invention is directed to method for making these CHO cell lines. This method involves transforming a CHO cell with DNA encoding GAA or a GAA variant, selecting a CHO cell that stably integrates the DNA encoding GAA into its chromosome(s) and that stably expresses GAA, and selecting a CHO cell that expresses GAA having a high content of glycans bearing M6P or bis-M6P, and, optionally, selecting a CHO cell having N-glycans with high sialic acid content and/or having N-glycans with a low non-phosphorylated high-mannose content.

These CHO cell lines may be used to produce rhGAA and rhGAA compositions according to the invention by culturing the CHO cell line and recovering said composition from the culture of CHO cells.

The rhGAA composition of the invention or its fractions or derivatives is advantageously used to treat subjects having a condition, disorder or disease associated with insufficient lysosomal GAA by administering the rhGAA composition. A subject in need of treatment includes those having Glycogen Storage Disease Type II (Pompe Disease) as well as other conditions, disorders or diseases which would benefit from the administration of the rhGAA.

The Examples below show that the rhGAA of the invention (ATB-200) is taken up by skeletal muscle cells, binds to CIMPR and effectively removes glycogen from skeletal muscle cells when administered at a significantly lower dosage than conventional rhGAA products. A reduction of up to 75% of glycogen in skeletal muscle myoblast was attained in GAA-knockout mice using a biweekly regimen of intravenous administration of ATB-200. These reductions exceeded those provided by the same amount of LUMIZYME® showing that the rhGAA of the invention, which has an enhanced content of N-glycans bearing M6P and bis-M6P, provided superior reductions in glycogen substrate. Due to the improved targeting, pharmacodynamics and pharmacokinetics of the rhGAA composition of the invention may be administered in a lower dosage than conventional rhGAA products such as LUMIZYME® or MYOZYME®.

It may be used to degrade, decrease or remove glycogen from cardiac muscle, smooth muscle, or striated muscle. Examples of skeletal or striated muscles subject to treatment include at least one muscle selected from the group consisting of abductor digiti minimi (foot), abductor digiti minimi (hand), abductor halluces, abductor pollicis brevis, abductor pollicis longus, adductor brevis, adductor halluces, adductor longus, adductor magnus, adductor pollicis, anconeus, articularis cubiti, articularis genu, aryepiglotticus, aryjordanicus, auricularis, biceps brachii, biceps femoris, brachialis, brachioradialis, buccinators, bulbospongiosus, constrictor of pharynx-inferior, constrictor of pharynx-middle, constrictor of pharynx-superior, coracobrachialis, corrugator supercilii, cremaster, cricothyroid, dartos, deep transverse perinei, deltoid, depressor anguli oris, depressor labii inferioris, diaphragm, digastric, digastric (anterior view), erector spinae-spinalis, erector spinae-iliocostalis, erector spinae-longissimus, extensor carpi radialis brevis, extensor carpi radialis longus, extensor carpi ulnaris, extensor digiti minimi (hand), extensor digitorum (hand), extensor digitorum brevis (foot), extensor digitorum longus (foot), extensor hallucis longus, extensor indicis, extensor pollicis brevis, extensor pollicis longus, external oblique abdominis, flexor carpi radialis, flexor carpi ulnaris, flexor digiti minimi brevis (foot), flexor digiti minimi brevis (hand), flexor digitorum brevis, flexor digitorum longus (foot), flexor digitorum profundus, flexor digitorum superficialis, flexor hallucis brevis, flexor hallucis longus, flexor pollicis brevis, flexor pollicis longus, frontalis, gastrocnemius, gemellus inferior, gemellus superior, genioglossus, geniohyoid, gluteus maximus, gluteus medius, gluteus minimus, gracilis, hyoglossus, iliacus, inferior oblique, inferior rectus, infraspinatus, intercostals external, intercostals innermost, intercostals internal, internal oblique abdominis, interossei-dorsal of hand, interossei-dorsal of foot, interossei-palmar of hand, interossei-plantar of foot, interspinales, intertransversarii, intrinsic muscles of tongue, ishiocavernosus, lateral cricoarytenoid, lateral pterygoid, lateral rectus, latissimus dorsi, levator anguli oris, levator ani-coccygeus, levator ani-iliococcygeus, levator ani-pubococcygeus, levator ani-puborectalis, levator ani-pubovaginalis, levator labii superioris, levator labii superioris, alaeque nasi, levator palpebrae superioris, levator scapulae, levator veli palatine, levatores costarum, longus capitis, longus colli, lumbricals of foot, lumbricals of hand, masseter, medial pterygoid, medial rectus, mentalis, m. uvulae, mylohyoid, nasalis, oblique arytenoid, obliquus capitis inferior, obliquus capitis superior, obturator externus, obturator internus (A), obturator internus (B), omohyoid, opponens digiti minimi (hand), opponens pollicis, orbicularis oculi, orbicularis oris, palatoglossus, palatopharyngeus, palmaris brevis, palmaris longus, pectineus, pectoralis major, pectoralis minor, peroneus brevis, peroneus longus, peroneus tertius, piriformis (A), piriformis (B), plantaris, platysma, popliteus, posterior cricoarytenoid, procerus, pronator quadratus, pronator teres, psoas major, psoas minor, pyramidalis, quadratus femoris, quadratus lumborum, quadratus plantae, rectus abdominis, rectus capitus anterior, rectus capitus lateralis, rectus capitus posterior major, rectus capitus posterior minor, rectus femoris, rhomboid major, rhomboid minor, risorius, salpingopharyngeus, sartorius, scalenus anterior, scalenus medius, scalenus minimus, scalenus posterior, semimembranosus, semitendinosus, serratus anterior, serratus posterior inferior, serratus posterior superior, soleus, sphincter ani, sphincter urethrae, splenius capitis, splenius cervicis, stapedius, sternocleidomastoid, sternohyoid, sternothyroid, styloglossus, stylohyoid, stylohyoid (anterior view), stylopharyngeus, subclavius, subcostalis, subscapularis, superficial transverse, perinei, superior oblique, superior rectus, supinator, supraspinatus, temporalis, temporoparietalis, tensor fasciae lata, tensor tympani, tensor veli palatine, teres major, teres minor, thyro-arytenoid & vocalis, thyro-epiglotticus, thyrohyoid, tibialis anterior, tibialis posterior, transverse arytenoid, transversospinalis-multifidus, transversospinalis-rotatores, transversospinalis-semispinalis, transversus abdominis, transversus thoracis, trapezius, triceps, vastus intermedius, vastus lateralis, vastus medialis, zygomaticus major, and zygomaticus minor.

The GAA composition of the invention may also be administered to, or used to treat, type 1 (slow twitch) muscle fiber or type 2 (fast twitch) muscle fiber or subjects accumulating glycogen in such muscle fibers. Type I, slow twitch, or "red" muscle, is dense with capillaries and is rich in mitochondria and myoglobin, giving the muscle tissue its characteristic red color. It can carry more oxygen and sustain aerobic activity using fats or carbohydrates as fuel. Slow twitch fibers contract for long periods of time but with little force. Type II, fast twitch muscle, has three major subtypes (IIa, IIx, and IIb) that vary in both contractile speed and force generated. Fast twitch fibers contract quickly and powerfully but fatigue very rapidly, sustaining only short, anaerobic bursts of activity before muscle contraction becomes painful. They contribute most to muscle strength and have greater potential for increase in mass. Type IIb is anaerobic, glycolytic, "white" muscle that is least dense in mitochondria and myoglobin. In small animals (e.g., rodents) this is the major fast muscle type, explaining the pale color of their flesh.

The rhGAA composition of the invention, its fractions or derivatives may be administered systemically, for example, by intravenous (IV) infusion, or administered directly into a desired site, such as into cardiac or skeletal muscle, such as quadriceps, triceps, or diaphragm. It may be administered to myocytes, particular muscle tissues, muscles, or muscle groups. For example, such a treatment may administer intramuscularly the rhGAA composition directly into a subject's quadriceps or triceps or diaphragm.

As mentioned above, the rhGAA composition of the invention, its fractions or derivatives can be complexed or admixed with a chaperone, such as AT-2220 (Duvoglustat HCl, 1-Deoxynojirimycin) or AT-2221(Miglustat, N-butyl-deoxynojirimycin) or their salts to improve the pharmacokinetics of the rhGAA administration. The rhGAA and the chaperone may be administered together or separately. When administered simultaneously the GAA in the composition may be preloaded with the chaperone. Alternatively, the GAA and the chaperone may be administered separately either at the same time or at different times.

Representative dosages of AT2221 range from 0.25 to 400 mg/kg, preferably from 0.5-200 mg/kg, and most preferably from 2 to 50 mg/kg. Specific dosages of AT2221 include 1, 2, 3, 4, 5, 10, 15, 20, 25, 30, 35, 40, 45 and 50 mg/kg. These dosages may be combined with rhGAA, such as ATB-200 rhGAA, at a molar ratio of AT2221 to rhGAA ranging from 15:1 to 150:1. Specific ratios include 15:1, 20:1, 25:1, 50:1, 60:1, 65:1, 70:1, 75:1, 80:1, 85:1, 90:1, 100:1, 125:1, and 150:1. rhGAA and AT2221 may be coadministered in these amounts or molar ratios either concurrently, sequentially or separately. The ranges above include all intermediate subranges and values, such as all integer values between the range endpoints.

Representative dosages of AT2220 range from 0.1 to 120 mg/kg, preferably 0.25 to 60, and most preferably from 0.6 to 15 mg/kg. Specific dosages of AT2220 include 1, 2, 3, 4, 5, 6, 7, 8, 9, 10, 15, 20, 25 and 30 mg/kg. These dosages may be combined with rhGAA, such as ATB-200 rhGAA, at a molar ratio of AT2220 to rhGAA ranging from 15:1 to 150:1. Specific ratios include 15:1, 20:125:1, 50:1, 60:1, 65:1, 70:1, 75:1, 80:1, 85:1, 90:1, 100:1, 125:1, and 150:1. rhGAA and AT2220 may be coadministered in these amounts or molar ratios either concurrently, sequentially or separately. The ranges above include all intermediate subranges and values, such as all integer values between the range endpoints.

The rhGAA composition of the invention, its fractions or derivatives may also be used for metabolizing, degrading, removing or otherwise decreasing glycogen in tissue, muscle, muscle fiber, muscle cells, lysosomes, organelles, cellular compartments, or cytoplasm. By administering the rhGAA composition to a subject, optionally along with a chaperone or a drug that reduces immunological responses to rhGAA.

In another embodiment of its method of use, the rhGAA of the invention may be used for modulating lysosomal proliferation, autophagy, or exocytosis in a cell by administering it, its fractions, or derivatives to cells, tissues, or subjects in need of such modulation, optionally in combination with a chaperone or optionally as a conjugate with another targeting moiety. Autophagy is a catabolic mechanism that allows a cell to degrade glycogen or other unnecessary or dysfunctional cellular components through the actions of it lysosomes. This method can also involve systemically or locally administering the GAA composition to a subject in need of treatment.

The rhGAA according to the invention, which is enriched for mono-M6P and bis-M6P, compared to LUMIZYME® and MYOZYME®, and which has favorable pharmacokinetic properties conferred by its glycosylation pattern may also be used for treatment of other conditions requiring the breakdown of complex carbohydrates, such as other disorders in which glycogen or other carbohydrates degraded by rhGAA accumulate in the lysosomes or other parts of the cell, such as in the cytoplasm accessible to rhGAA, such as Glycogen storage disease III. It may also be used non-therapeutic purposes, such as for the production of foods, beverages, chemicals and pharmaceutical products which require breaking down complex carbohydrates such as starch and glycogen into their monomers.

Examples

The following non-limiting Examples exemplify aspects of the invention.

Section I: ATB-200 rhGAA and its Properties
Limitations of Existing MYOZYME® and LUMIZYME® rhGAA Products To evaluate the ability of the rhGAA in MYOZYME® and LUMIZYME®, the only currently approved treatments for Pompe disease, these rhGAA preparations were injected onto a CIMPR column (which binds rhGAA having M6P groups) and subsequently eluted with a free M6 gradient. Fractions were collected in 96-well plate and GAA activity assayed by 4MU-α-glucose substrate. The relative amounts of bound and unbound rhGAA were determined based on GAA activity and reported as the fraction of total enzyme.

Figures 2A, 2B:
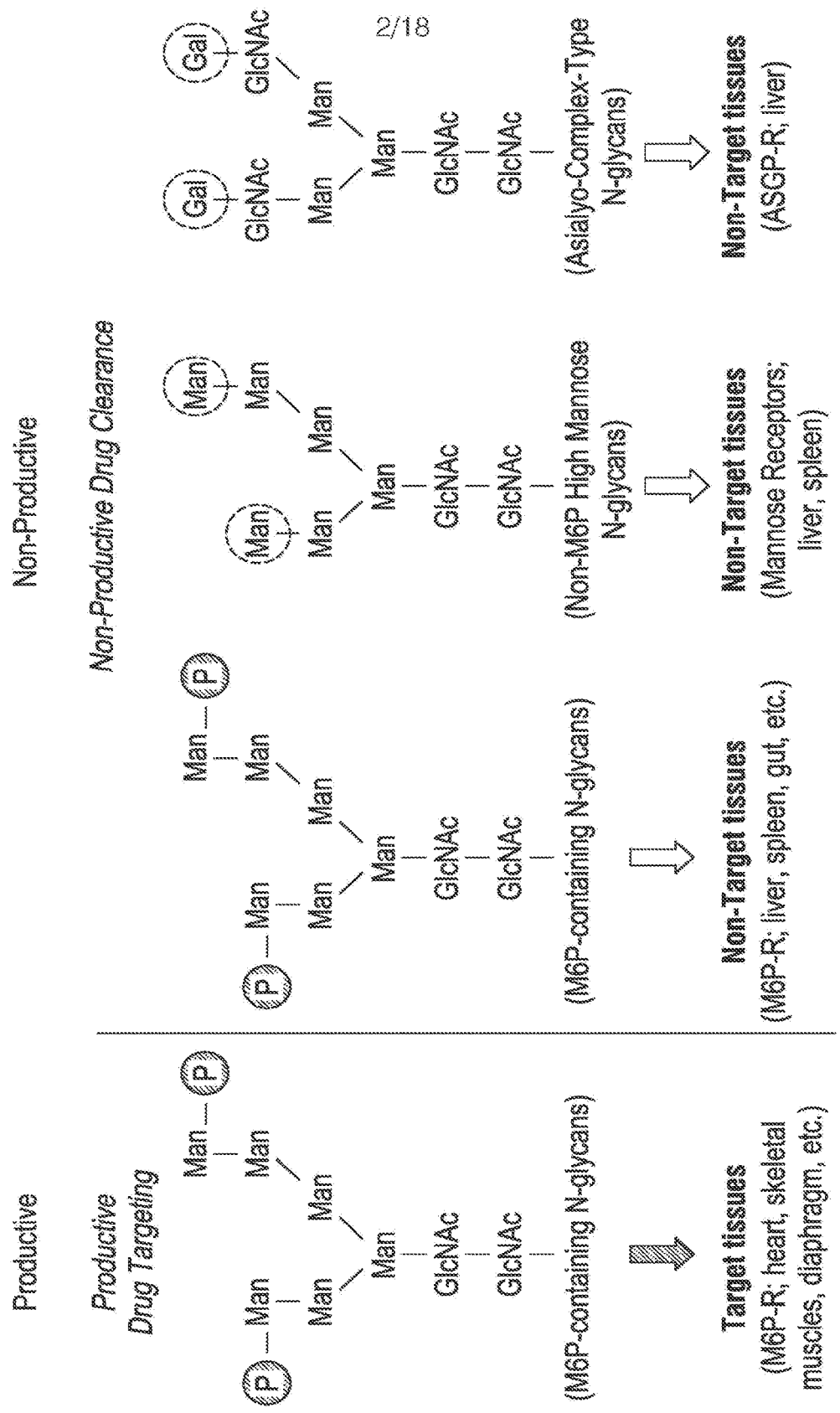
FIG. 2A describes productive targeting of rhGAA via glycans bearing M6P to target tissues (e.g., muscle tissues of subject with Pompe Disease).
FIG. 2B describes non-productive drug clearance to non-target tissues (e.g., liver and spleen) or by binding of non-M6P glycans to non-target tissues.
Figure 4A:
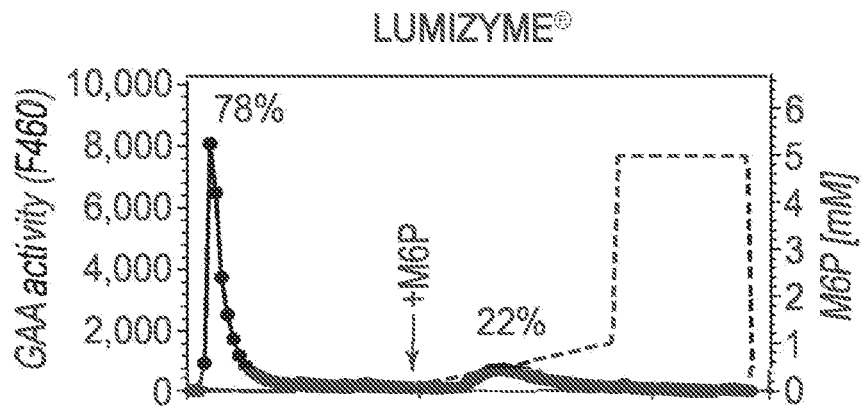
FIGS. 4A and 4B, respectively, show the results of CIMPR affinity chromatography of LUMIZYME® and MYOZYME®. The dashed lines refer to the M6P elution gradient. Elution with M6P displaces GAA molecules bound via an M6P-containing glycan to CIMPR.
Figure 4B:
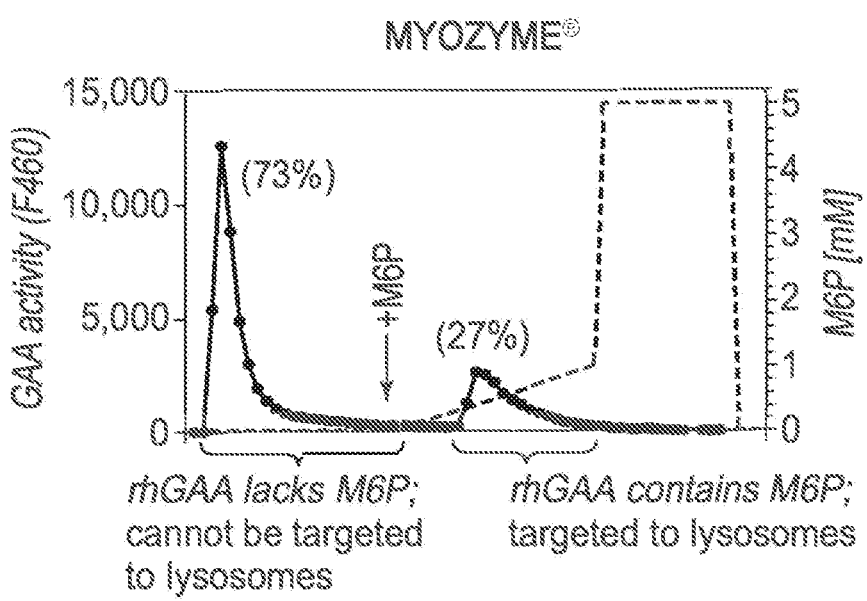

FIGS. 4A and 4B describe the problems associated with conventional ERTs (MYOZYME® and LUMIZYME®): 73% of the rhGAA in MYOZYME® (FIG. 4B) and 78% of the rhGAA in LUMIZYME® (FIG. 4A) did not bind to the CIMPR, see the left-most peaks in each figure. Only 27% of the rhGAA in MYOZYME® and 22% of the rhGAA in LUMIZYME® contained M6P that can productive target it to the CIMPR on muscle cells, see FIG. 2 which describes productive drug targeting and non-productive drug clearance.

An effective dose of MYOZYME® and LUMIZYME® corresponds to the amount of rhGAA containing M6P which targets the CIMPR on muscle cells. However, most of the rhGAA in these two conventional products does not target the CIMPR receptor on target muscle cells. The administration of a conventional rhGAA where most of the rhGAA is not targeted to muscle cells increases the risk of allergic reaction or induction of immunity to the non-targeted rhGAA.

Preparation of CHO Cells Producing ATB-200 rhGAA Having a High Content of Mono- or Bis-M6P-Bearing N-Glycans.

Figure 5:
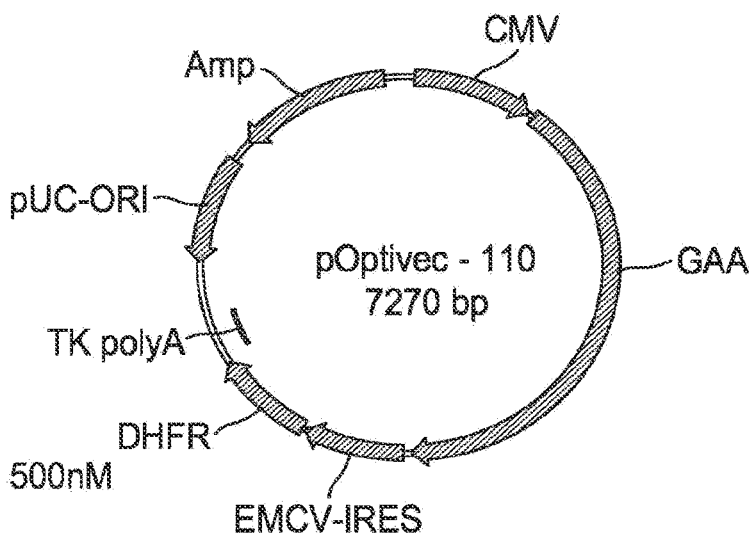
FIG. 5. shows a DNA construct for transforming CHO cells with DNA encoding rhGAA. CHO cells were transformed with a DNA construct encoding rhGAA (SEQ ID NO: 2).

CHO cells were transfected with DNA that expresses rh-GAA followed by selection of transformants producing rhGAA. A DNA construct for transforming CHO cells with DNA encoding rh-GAA is shown in FIG. 5. CHO cells were transfected with DNA that expresses rh-GAA followed by selection of transformants producing rhGAA.

After transfection, DG44 CHO (DHFR-) cells containing a stably integrated GAA gene were selected with hypoxanthine/thymidine deficient (-HT) medium). Amplification of GAA expression in these cells was induced by methotrexate treatment (MTX, 500 nM). Cell pools that expressed high amounts of GAA were identified by GAA enzyme activity assays and were used to establish individual clones producing rhGAA. Individual clones were generated on semisolid media plates, picked by CLONEPIX™ system, and were transferred to 24-deep well plates. The individual clones were assayed for GAA enzyme activity to identify clones expressing a high level of GAA. Conditioned media for determining GAA activity used a 4-MU-α-Glucosidase substrate. Clones producing higher levels of GAA as measured by GAA enzyme assays were further evaluated for viability, ability to grow, GAA productivity, N-glycan structure and stable protein expression. CHO cell lines, including CHO cell line GA-ATB-200, expressing rhGAA with enhanced mono-M6P or bis-M6P N-glycans were isolated using this procedure.

Purification of rhGAA ATB-200 rhGAA

Figure 6A:
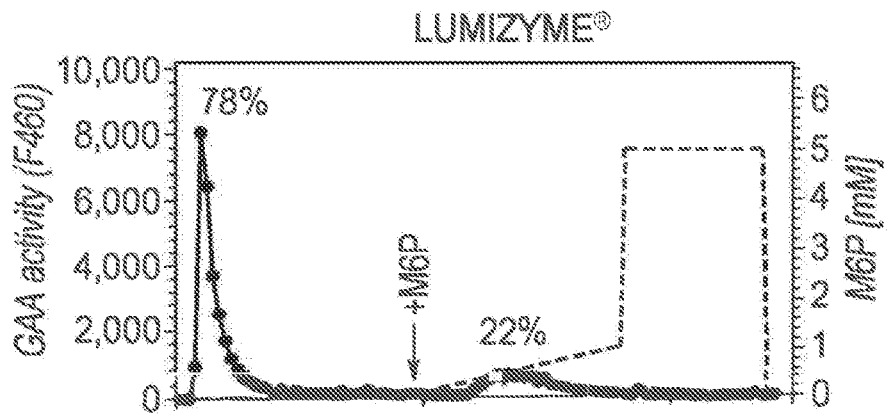
FIGS. 6A and 6B show the results of CIMPR affinity chromatography of LUMIZYME® and ATB-200 rhGAA. As apparent from FIG. 6B, about 70% of the rhGAA in ATB-200 rhGAA contained M6P.
Figure 6B:
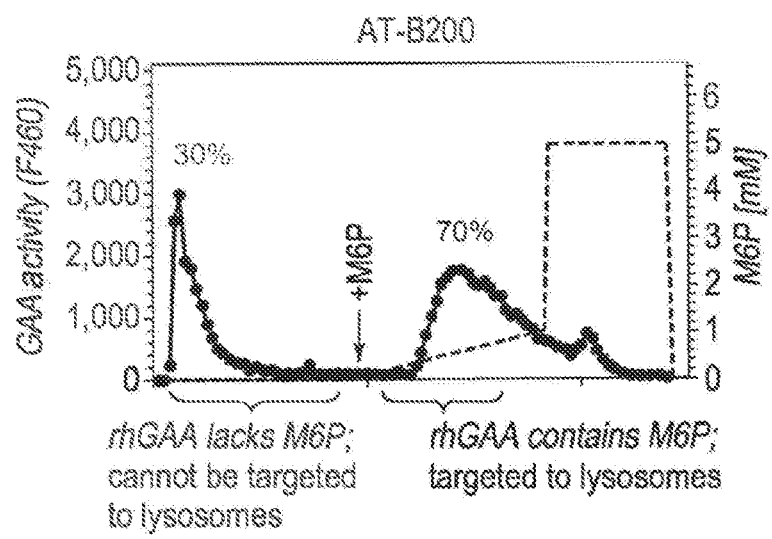
Figure 7A:
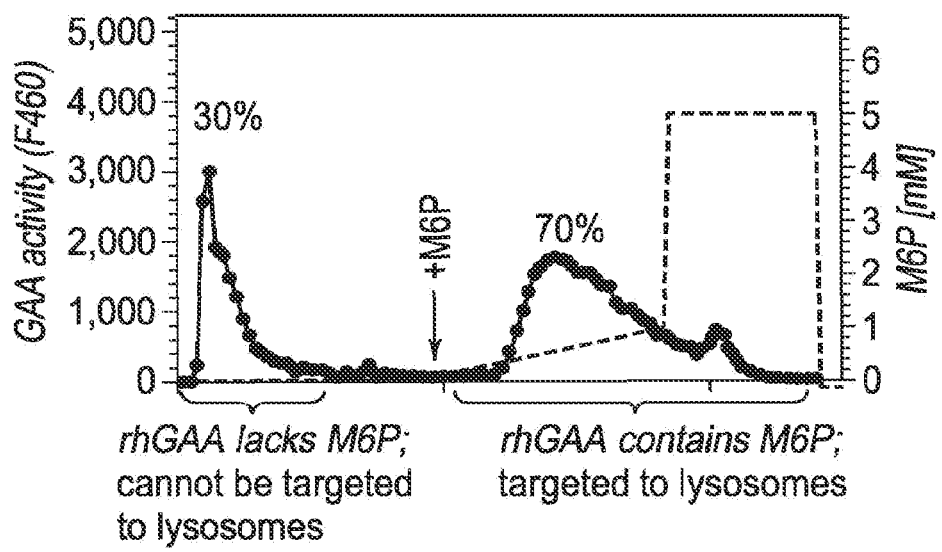
FIGS. 7A-7B show ATB-200 rhGAA purification, Embodiments 1 & 2.
Figure 7B:
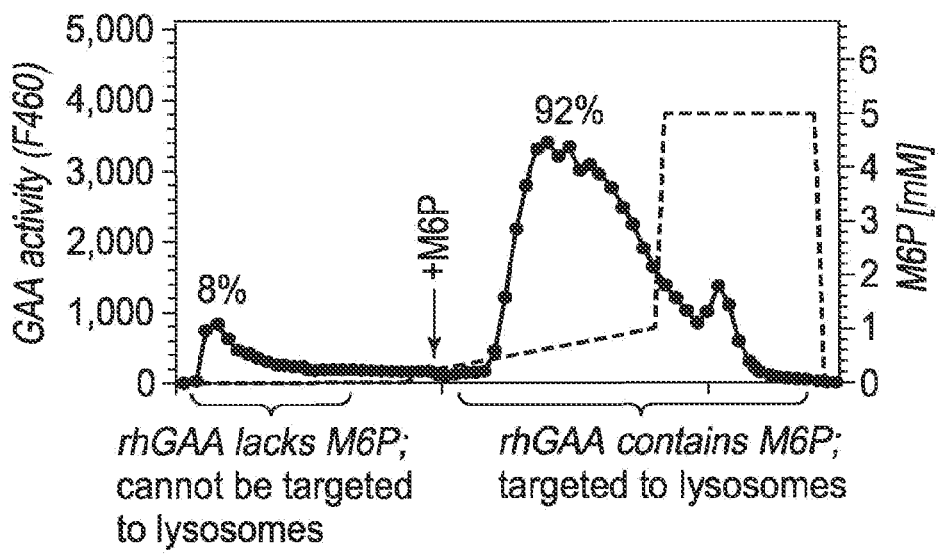

Multiple batches of the rhGAA according to the invention were produced in shake flasks and in perfusion bioreactors using CHO cell line GA-ATB-200 and CIMPR binding was measured. Similar CIMPR receptor binding (~70%) to that shown in FIG. 6B and FIG. 7 was observed for purified ATB-200 rhGAA from different production batches indicating that ATB-200 rhGAA can be consistently produced. As shown by FIGS. 6A and 6B, LUMIZYME® rhGAA exhibited significantly less CIMPR binding than ATB-200 rhGAA.

Analytical Comparison of ATB-200 to LUMIZYME®

Figure 8:
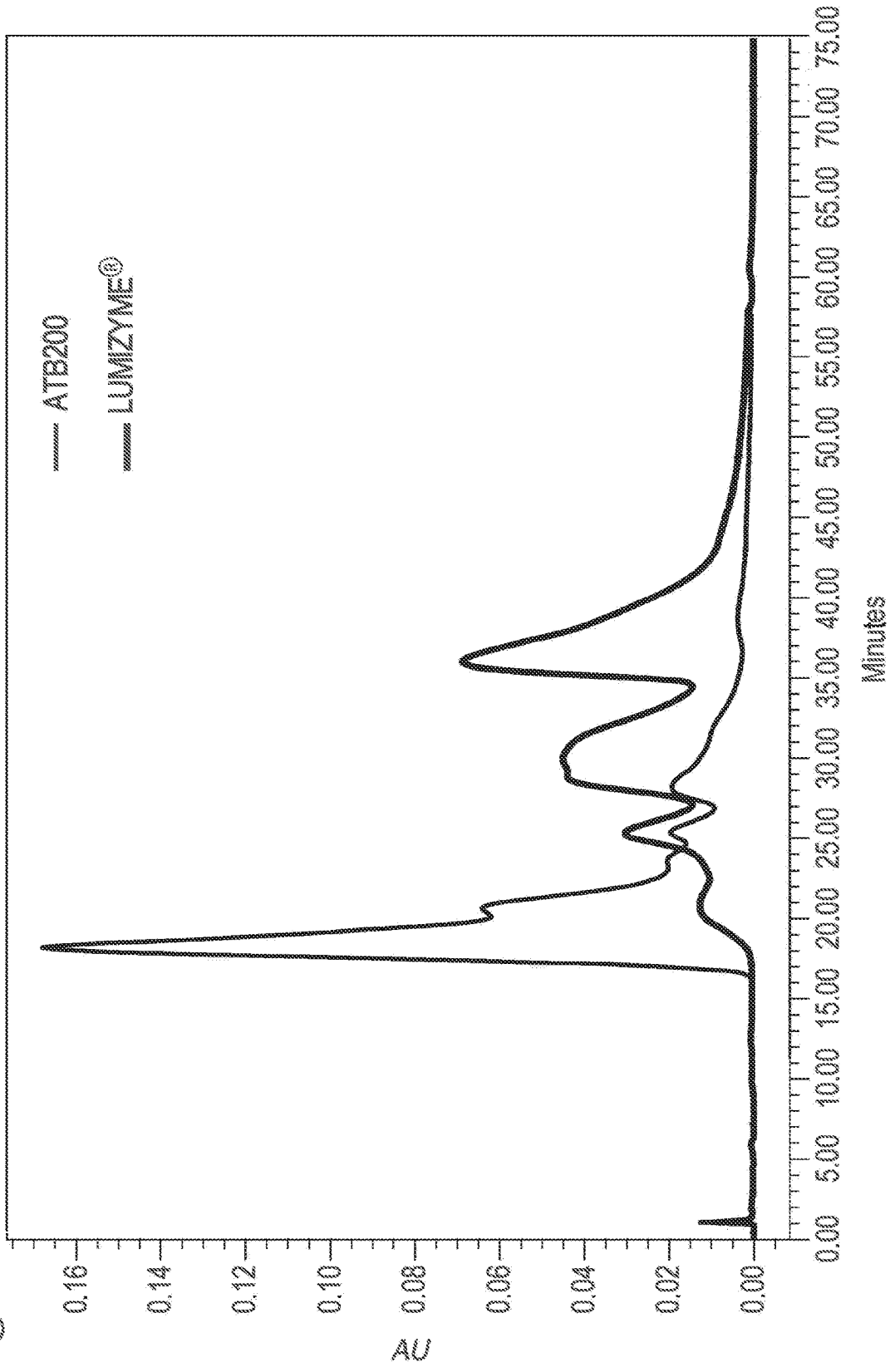
FIG. 8 shows Polywax elution profiles of LUMIZYME® and ATB-200 rhGAAs.

Weak anion exchange ("WAX") liquid chromatography was used to fractionate ATB-200 rhGAA according to terminal phosphate. Elution profiles were generated by eluting the ERT with increasing amount of salt. The profiles were monitored by UV (A280 nm). ATB-200 rhGAA was obtained from CHO cells and purified. LUMIZYME® was obtained from a commercial source. LUMIZYME® exhibited a high peak on the left of its elution profile. ATB-200 rhGAA exhibited four prominent peaks eluting to the right of LUMIZYME® (FIG. 8). This confirms that ATB-200 rhGAA was phosphorylated to a greater extent than LUMIZYME® since this evaluation is by terminal charge rather than CIMPR affinity.

Oligosaccharide Characterization of ATB-200 rhGAA

Purified ATB-200 rhGAA and LUMIZYME® glycans were evaluated by MALDI-TOF to determine the individual glycan structures found on each ERT (FIG. 9). ATB-200 samples were found to contain slightly lower amounts of non-phosphorylated high-mannose type N-glycans than LUMIZYME®. The higher content of M6P glycans in ATB-200 than in LUMIZYME®, targets ATB-200 rhGAA to muscle cells more effectively. The high percentage of mono-phosphorylated and bis-phosphorylated structures determined by MALDI agree with the CIMPR profiles which illustrated significantly greater binding of ATB-200 to the CIMPR receptor. N-glycan analysis via MALDI-TOF mass spectrometry confirmed that on average each ATB200 molecule contains at least one natural bis-M6P N-glycan structure. This higher bis-M6P N-glycan content on ATB-200 rhGAA directly correlated with high-affinity binding to CIMPR in M6P receptor plate binding assays ($K_D$ about 2-4 nM) (FIG. 10A).

Characterization of CIMPR Affinity of ATB-200

In addition to having a greater percentage of rhGAA that can bind to the CIMPR, it is important to understand the quality of that interaction. LUMIZYME® and ATB200 rhGAA receptor binding was determined using a CIMPR plate binding assay. Briefly, CIMPR-coated plates were used to capture GAA. Varying concentrations of rhGAA were applied to the immobilized receptor and unbound rhGAA was washed off. The amount of remaining rhGAA was determined by GAA activity. As shown by FIG. 10A, ATB-200 rhGAA bound to CIMPR significantly better than LUMIZYME®.

Figures 10A, 10B:
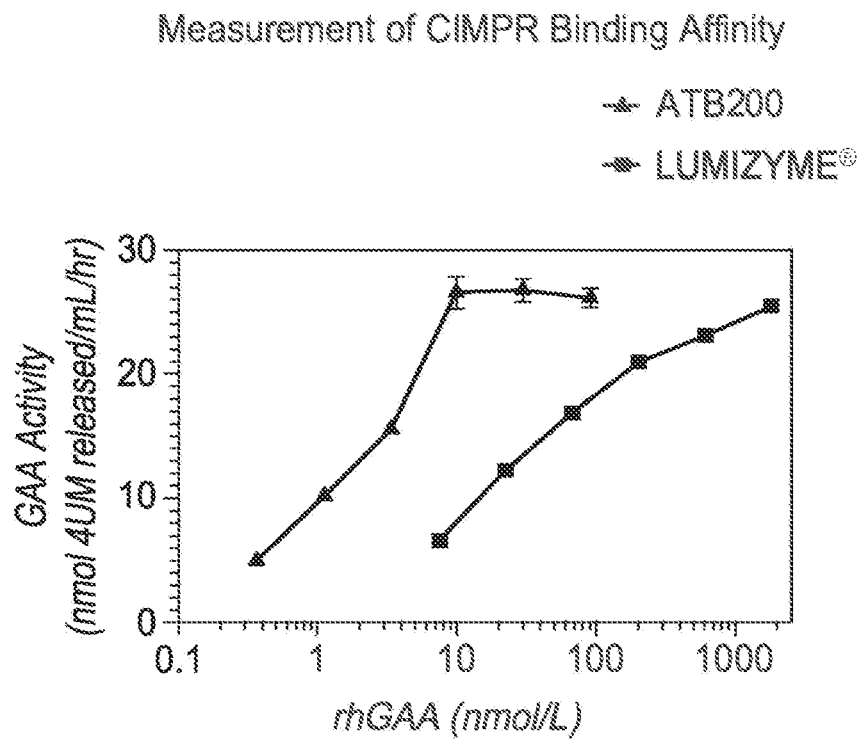
FIG. 10A compares the CIMPR binding affinity of ATB-200 rhGAA (left trace) with that of LUMIZYME® (right trace).
FIG. 10B describes the Bis-M6P content of LUMIZYME® and ATB-200 rhGAA.

FIG. 10B shows the relative content of bis-M6P glycans in LUMIZYME®, a conventional rhGAA, and ATB-200 according to the invention. For LUMIZYME® there is on average only 10% of molecules have a bis-phosphorylated glycan. Contrast this with ATB-200 where on average every rhGAA molecule has at least one bis-phosphorylated glycan.

ATB-200 rhGAA was More Efficiently Internalized by Fibroblast than LUMIZYME®

The relative cellular uptake of ATB-200 and LUMIZYME® rhGAA were compared using normal and Pompe fibroblast cell lines. Comparisons involved 5-100 nM of ATB-200 rhGAA according to the invention with 10-500 nM conventional rhGAA TRIS base and cells were washed 3-times with PBS prior to harvest. Internalized GAA measured by 4MU-α-Glucoside hydrolysis and was graphed relative to total cellular protein and the results appear in FIG. 11.

ATB-200 rhGAA was also shown to be efficiently internalized into cells (FIGS. 11A and 11B, respectively), show that ATB-200 rhGAA is internalized into both normal and Pompe fibroblast cells and that it is internalized to a greater degree than conventional LUMIZYME® rhGAA. ATB-200 rhGAA saturates cellular receptors at about 20 nM, while about 250 nM of LUMIZYME® is needed. The uptake efficiency constant ($K_{uptake}$) extrapolated from these results is 2-3 nm for ATB-200 and 56 nM for LUMIZYME® as shown by FIG. 11C. These results suggest that ATB-200 rhGAA is a well-targeted treatment for Pompe disease.

Section II: Preclinical Studies

ATB-200 rhGAA with Superior Glycosylation was Significantly Better than Standard of Care ERT for Glycogen Clearance in Skeletal Muscles of GAA KO Mice As explained above, enzyme replacement therapy (ERT) using recombinant human GAA (rhGAA) is the only approved treatment available for Pompe disease. This ERT requires the specialized carbohydrate mannose 6-phosphate (M6P) for cellular uptake and subsequent delivery to lysosomes via cell surface cation-independent M6P receptors (CIMPRs). However, the current rhGAA ERT contains low amounts of M6P that limit drug targeting and efficacy in disease-relevant tissues. The inventors developed a production cell line and manufacturing process that yield rhGAA (designated as ATB-200 rhGAA) with superior glycosylation and higher M6P content than conventional rhGAA, particularly the high-affinity bis-M6P N-glycan structure, for improved drug targeting. ATB-200 rhGAA binds the CI-MPR with high affinity (KD~2-4 nM) and was efficiently internalized by Pompe fibroblasts and skeletal muscle myoblasts ($K_{uptake}$~7-14 nM).

Figure 12A:
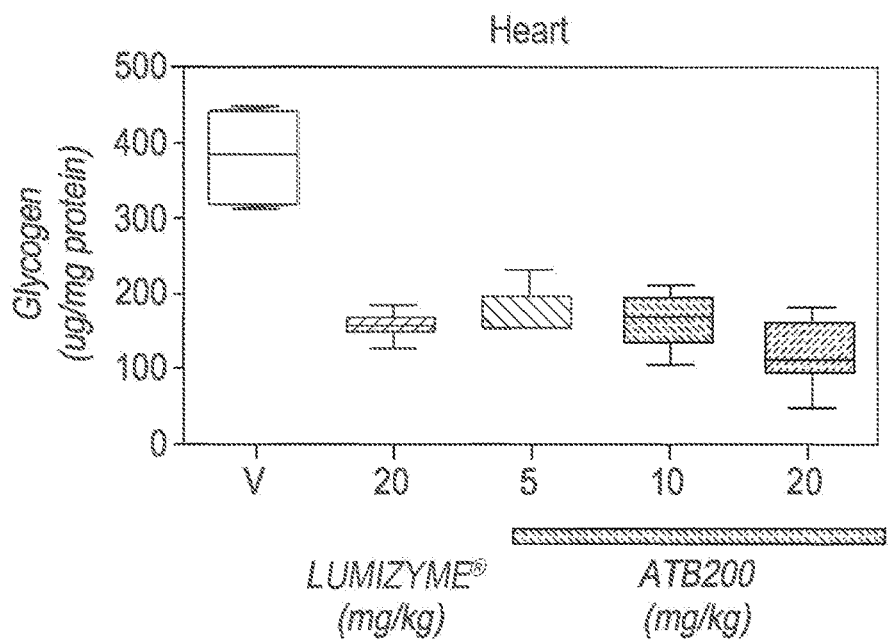
FIG. 12A shows the amount of glycogen relative to protein in heart muscle after contact with vehicle (negative control), with 20 mg/ml LUMIZYME®, or with 5, 10 or 20 mg/kg ATB-200 rhGAA.
Figure 12B:
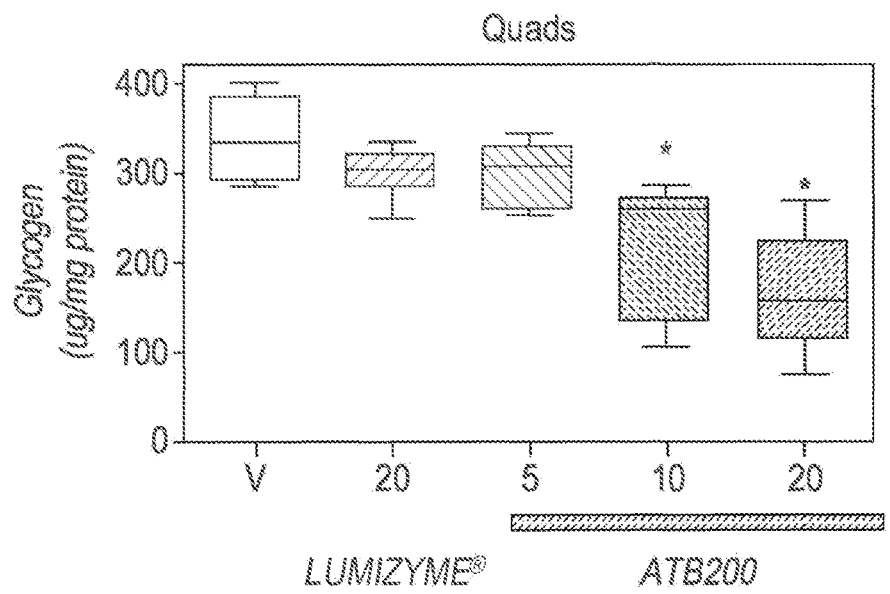
FIG. 12B shows the amount of glycogen relative to protein in quadriceps muscle after contact with vehicle (negative control), with 20 mg/ml LUMIZYME®, or with 5, 10 or 20 mg/kg ATB-200 rhGAA.
Figure 12C:
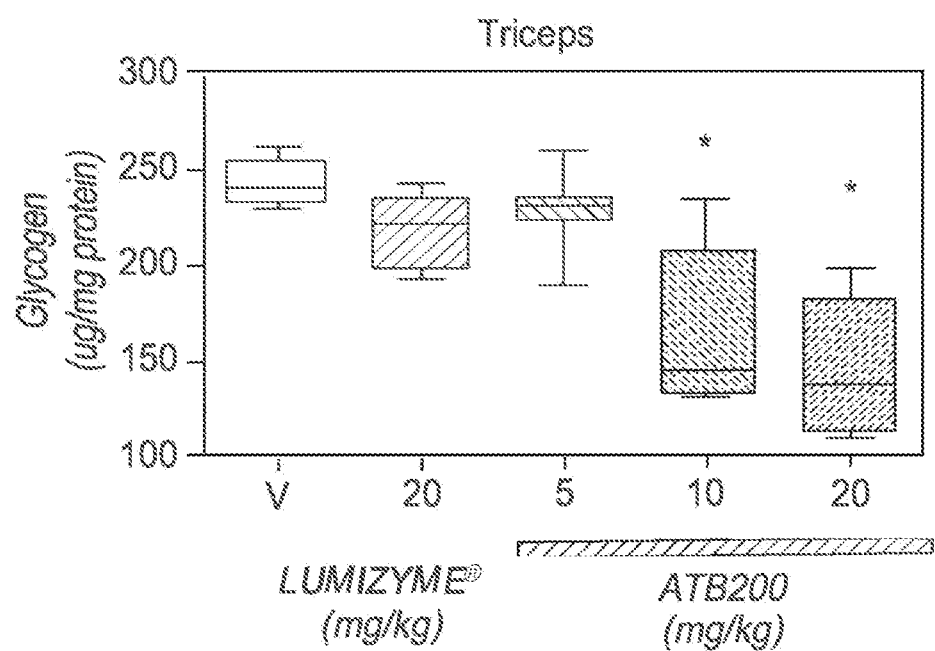
FIG. 12C shows the amount of glycogen relative to protein in triceps muscle after contact with vehicle (negative control), with 20 mg/ml LUMIZYME®, or with 5, 10 or 20 mg/kg ATB-200 rhGAA. ATB-200 rhGAA produced significant glycogen reductions in quadriceps and triceps muscle compared to the negative control and compared to LUMIZYME®.

ATB-200 rhGAA clears glycogen significantly better than LUMIZYME® in skeletal muscle. The effects of administering LUMIZYME® and ATB-200 rhGAA for glycogen clearance in GAA KO mice were evaluated. Animals were given two IV bolus administrations (every other week); tissues were harvested two weeks after the last dose and analyzed for GAA activity and glycogen content (FIG. 12). ATB-200 rhGAA and LUMIZYME® rhGAA were equally effective for clearing glycogen in heart (FIG. 12A). As show in in FIGS. 12B and 12C, ATB-200 rhGAA at 5 mg/kg was equivalent to LUMIZYME® rhGAA at 20 mg/kg for reducing glycogen in skeletal muscles; ATB-200 dosed at 10 and 20 mg/kg was significantly better than LUMIZYME® for clearing glycogen in skeletal muscles.

Rationale for Co-Administration of ATB-200 rhGAA with AT2221 (CHART Technology)

Figures 13A, 13B:
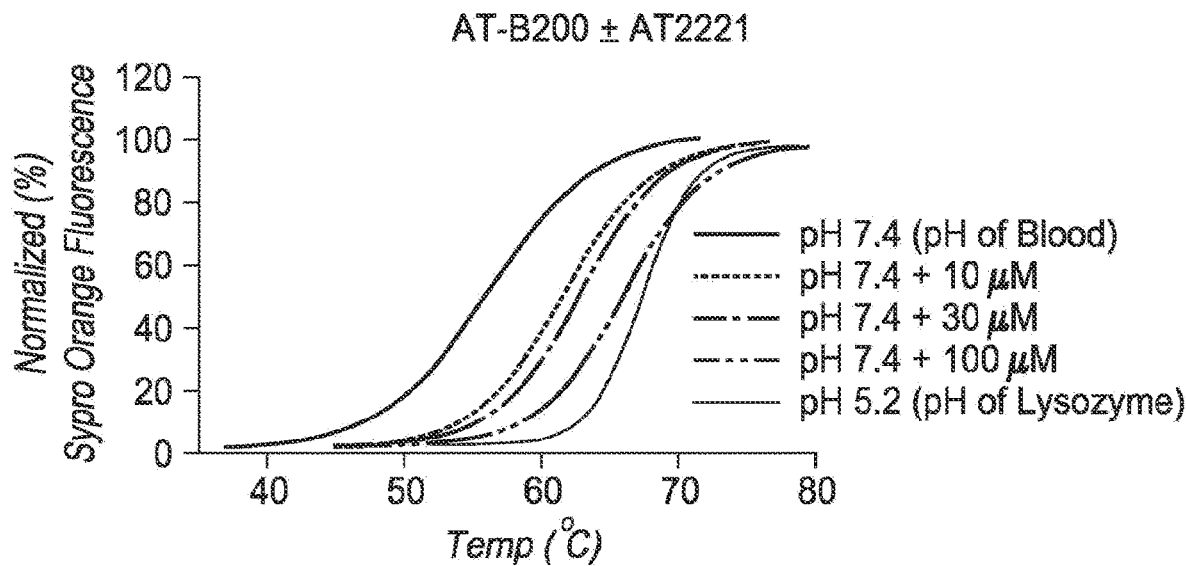
FIGS. 13A-13B show that ATB-200 rhGAA stability is improved in the presence of chaperone AT2221. The first, left trace in FIG. 13A shows percentage of unfolded ATB-200 rhGAA protein at various temperatures at pH 7.4 (blood pH). The last, right trace shows percentage of unfolded ATB-200 rhGAA protein at various temperatures at pH 5.2 (lysosome pH). The three intermediate traces show the effects of 10 µg, 30 µg, or 100 µg of AT2221 chaperone on protein folding. These data show that AT2221 prevents unfolding of ATB-200 rhGAA at blood pH compared to the control sample. The improvement of Tm at neutral pH by AT2221 is summarized in FIG. 13B.

A chaperone binds to and stabilizes rhGAA ERT, increases uptake of active enzyme into tissues, improves tolerability and potentially mitigates immunogenicity. As shown above, the protein stability of ERT under unfavorable conditions was substantially improved using CHART™ (CHART: chaperone-advanced replacement therapy). As shown by FIGS. 13A and 13B, the stability of ATB-200 was significantly improved by AT2221 (Miglustat, N-butyl-deoxynojirimycin). Folding of rhGAA protein was monitored at 37° C. by thermal denaturation in neutral (pH 7.4—plasma environment) or acidic (pH 5.2—lysosomal environment) buffers. AT2220 stabilized rhGAA protein in neutral pH buffer over 24 hours.

Figures 14, 15:
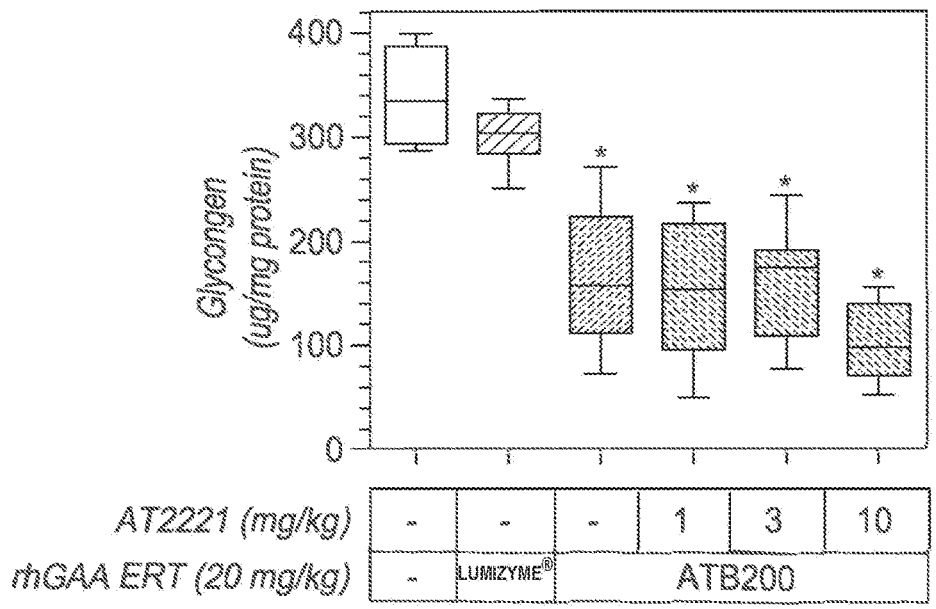
FIG. 14 shows that the combination of ATB-200 rhGAA and chaperone AT2221 provided significantly better glycogen clearance in GAA knock-out mice than treatments with LUMIZYME® and AT2221 or controls of either LUMIZYME® or ATB200 rhGAAs without the AT2221 chaperone.
FIG. 15 shows residual glycogen in quadriceps muscle after treatment with LUMIZYME®, ATB-200 rhGAA, or ATB-200 rhGAA and various concentrations of the AT2221 chaperone.

Co-Administration of LUMIZYME® with AT2221 (Miglustat) Compared to Co-Administration of ATB-200 rhGAA with Miglustat Twelve week old GAA KO mice treated with LUMIZYME® or ATB200, 20 mg/kg IV every other week 4 injections; Miglustat was co-administered at 10 mg/kg PO, 30 min prior to rhGAA as indicated. Tissues were collected 14 days after last enzyme dose for glycogen measurement. FIG. 14 shows the relative reduction of glycogen in quadriceps and triceps skeletal muscle.

Reduction of Tissue Glycogen with ATB-200 rhGAA Coadministered with Pharmacological Chaperone AT2221 (Miglustat).

The combination of a pharmacological chaperone and ATB-200 rhGAA was found to enhance glycogen clearance in vivo. GAA KO mice were given two IV bolus administrations of rhGAA at 20 mg/kg every other week. The pharmacological chaperone AT2221 was orally administered 30 mins prior to rhGAA at dosages of 0, 1, 2 and 10 mg/kg. Tissues were harvested two weeks after the last dose of ERT and analyzed for GAA activity, glycogen content cell specific glycogen and lysosome proliferation.

As shown by FIG. 15, the animals receiving ATB200+ chaperone AT2221 exhibited enhanced glycogen clearance from quadriceps muscle. ATB-200 rhGAA (20 mg/kg) reduced glycogen more than the same dose of LUMIZYME® and when ATB-200 rhGAA was combined with 10 mg/kg of AT2220 near normal levels of glycogen in muscle were attained.

Figure 16A:
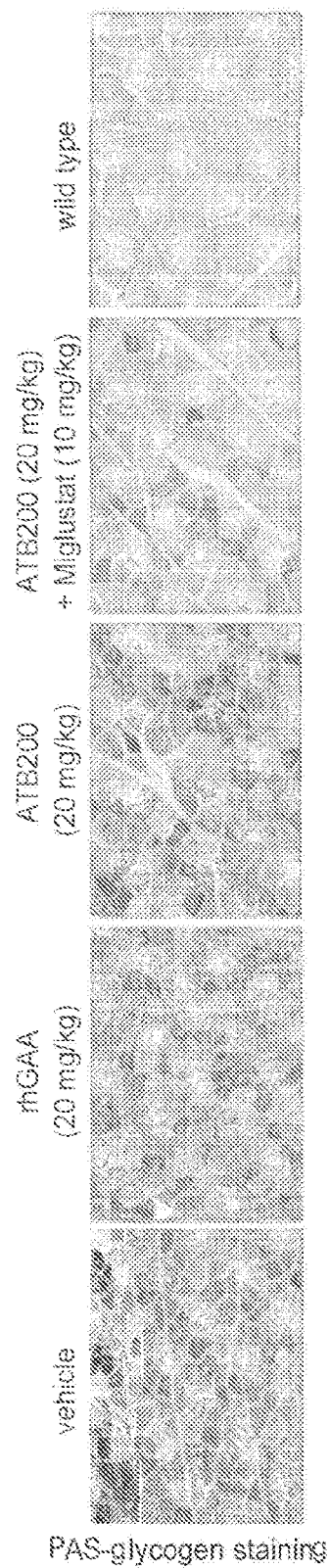
FIGS. 16A-16D show improvement of Skeletal Muscle Pathology in Mice treated with ATB200+Miglustat (AT2221) over those treated with ERT alone. PAS glycogen staining (FIG. 16A) and EM (FIG. 16B) of muscle tissue from GAA KO mice treated with conventional rhGAA or ATB-200 rhGAA and miglustat (AT-2221).
Figure 16B:
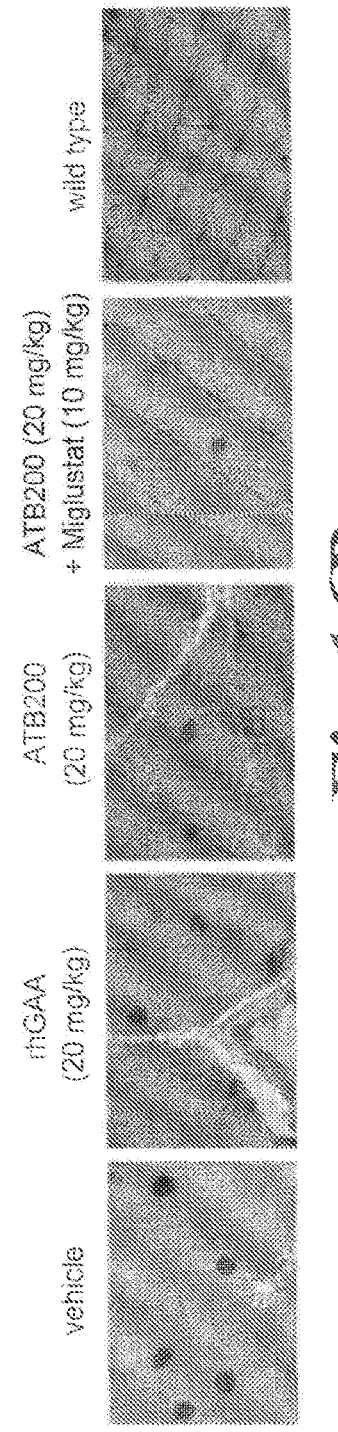

As shown by FIGS. 16A and 16B, unlike conventional rhGAA, which showed limited glycogen reduction (indicated by abundant punctate PAS signal), ATB-200 rhGAA alone showed a significant decrease in PAS signals. Co-administration with 10 mg/kg miglustat resulted in a substantial further reduction in substrate. TEM revealed that the majority of glycogen in the lysosomes as membrane-bound, electron-dense material, which correspond to the punctate PAS signals. Co-administration of ATB-200 rhGAA with miglustat, reduced the number, size and density of substrate-containing lysosomes suggesting targeted delivery of ATB-200 rhGAA to the muscle cells and subsequent delivery to the lysosomes.

Figure 16C:
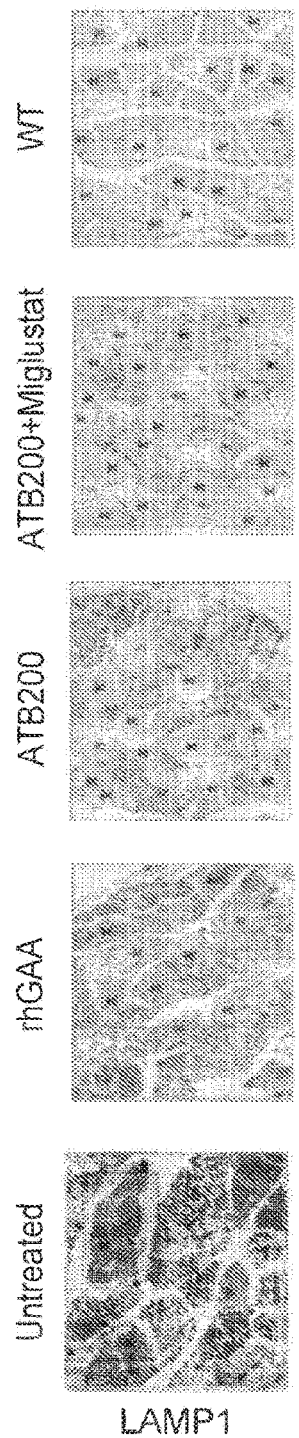

From the study (2 IV bolus every other week injections) shown above, tissues were processed for lysosomal proliferation using a LAMP 1 marker, the up-regulation is another hallmark of Pompe disease. LAMP: lysosome-associated membrane protein. From the study (2 IV bolus EOW injections) shown above, soleus tissue was processed for LAMP 1 staining in adjacent sections and type I fiber-specific antibody (NOQ7.5.4D) in adjacent sections (FIGS. 16C and 16D) ATB-200 rhGAA results in a more substantial LAMP1 reduction compared to conventional rhGAA, with reductions leading to levels seen in WT animals (FIG. 16C).

Figure 16D:
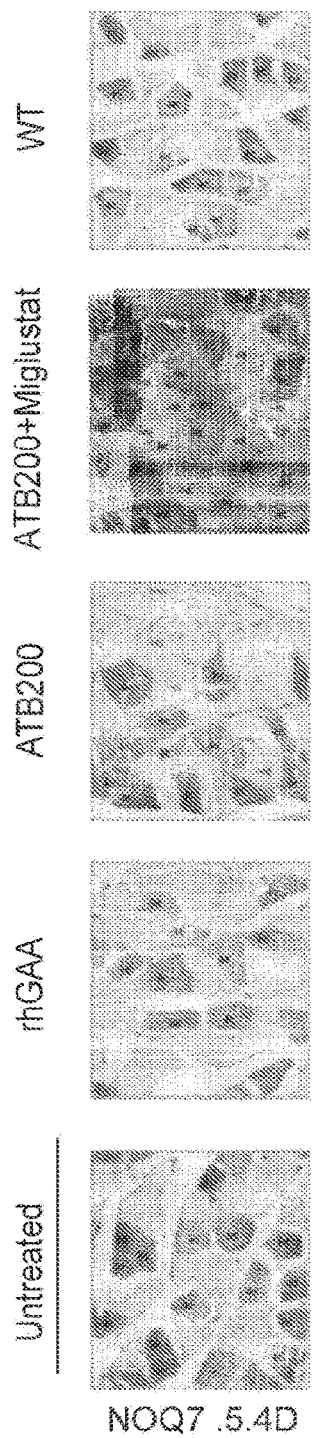

In addition, unlike rhGAA, where the effect is mostly restricted to type I fibers (slow twitch, marked with asterisks), ATB-200 rhGAA also led to significant reduction in LAMP1 signals in a fraction of type II (fast twitch) fibers (arrow heads) (FIG. 16D). Importantly, co-administration with miglustat further improved ATB-200-mediated reduction of LAMP1 proliferation in the majority of type II fibers (FIGS. 16C and 16D). As a result, there did not appear to be a significant fiber type-specific difference in the level of LAMP1 signals. Similar conclusions were drawn from quadriceps and diaphragm (data not shown).

In a separate and similarly designed study, the effect of ATB-200±AT2221 was examined over a longer term with 4 biweekly IV bolus injections. In heart, the main glycogen store in the cardiomyocytes was readily cleared by repeat administration of either rhGAA or ATB-200 to levels seen in wild-type (WT) animals (FIG. 17A). However, the substrate in cardiac smooth muscle cells seems to be cleared preferably by ATB-200 rhGAA, suggesting a potentially broader bio-distribution of ATB-200 compared to rhGAA (asterisks mark the lumen of cardiac blood vessels). Importantly, co-administration with miglustat further improved ATB-200-mediated reduction of LAMP1 proliferation.

These results show that ATB-200 rhGAA, which has higher levels of M6P and bis-M6P on its N-glycans efficiently targets CIMPR in skeletal muscle. ATB-200 rhGAA also has well-processed complex-type N-glycans that minimize non-productive clearance in vivo, has pharmacokinetic properties favorable for its use in vivo and exhibits good targeting to key muscle tissues in vivo. They also show that ATB-200 rhGAA is better than the conventional standard of care, LUMIZYME®, for reducing glycogen in muscle tissue and that a combination of ATB-200 rhGAA and chaperone AT2221 further improve removal of glycogen from target tissues and improves muscle pathology.

What is claimed is:

1. A composition comprising recombinant human alpha glucosidase (rhGAA), wherein 40%-60% of the N-glycans on the rhGAA are complex type N-glycans, and wherein each rhGAA molecule on average comprises at least one bis-phosphorylated mannose-6-phosphate (bis-M6P glycan).

2. The composition of claim 1, wherein at least 17% of the total glycans on the rhGAA are bis-M6P glycans.

3. The composition of claim 1, wherein the rhGAA comprises the amino acid sequence that is at least 90% identical to SEQ ID NO: 4.

4. The composition of claim 1, wherein the rhGAA comprises at least 3.0 mol mannose-6-phosphate (M6P) residues per mol rhGAA.

5. The composition of claim 4, wherein the rhGAA comprises at least 4.0 mol M6P residues per mol rhGAA.

6. The composition of claim 4, wherein the rhGAA comprises at least 5.0 mol M6P residues per mol rhGAA.

7. The composition of claim 4, wherein the rhGAA comprises at least 6.0 mol M6P residues per mol rhGAA.

8. The composition of claim 4, wherein the rhGAA comprises at least 7.0 mol M6P residues per mol rhGAA.

9. The composition of claim 4, wherein the rhGAA comprises from 3.0 mol to 6.0 mol M6P residues per mol rhGAA.

10. The composition of claim 4, wherein the rhGAA comprises from 3.0 mol to 7.0 mol M6P residues per mol rhGAA.

11. A pharmaceutical composition comprising the rhGAA of claim 1 and at least one pharmaceutically acceptable carrier or excipient.

12. The pharmaceutical composition of claim 11, wherein the pharmaceutically acceptable carrier is water.

13. The pharmaceutical composition of claim 11, wherein the composition is in the form of a lyophilized powder.

14. The pharmaceutical composition of claim 11, wherein the composition comprises mannitol.

15. The pharmaceutical composition of claim 11, wherein the composition comprises polysorbate 80.

16. The pharmaceutical composition of claim 11, wherein the composition comprises a pH buffer.

* * * * *